(12) United States Patent
Kusumoto et al.

(10) Patent No.: US 11,833,151 B2
(45) Date of Patent: Dec. 5, 2023

(54) PHARMACEUTICAL COMPOSITION INCLUDING SODIUM ALKYL SULFATE

(71) Applicant: TAIHO PHARMACEUTICAL CO., LTD., Tokyo (JP)

(72) Inventors: Kenji Kusumoto, Tokushima (JP); Sadahiro Miyamura, Tokushima (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 232 days.

(21) Appl. No.: 16/982,377

(22) PCT Filed: Mar. 18, 2019

(86) PCT No.: PCT/JP2019/011251
§ 371 (c)(1),
(2) Date: Sep. 18, 2020

(87) PCT Pub. No.: WO2019/181876
PCT Pub. Date: Sep. 26, 2019

(65) Prior Publication Data
US 2021/0030755 A1    Feb. 4, 2021

(30) Foreign Application Priority Data

Mar. 19, 2018 (JP) ................. 2018-051620

(51) Int. Cl.
| A61K 31/519 | (2006.01) |
| A61K 9/00 | (2006.01) |
| A61K 9/14 | (2006.01) |
| A61K 9/48 | (2006.01) |
| A61K 47/12 | (2006.01) |
| A61K 47/20 | (2006.01) |
| A61K 47/26 | (2006.01) |
| A61K 47/38 | (2006.01) |

(52) U.S. Cl.
CPC .......... *A61K 31/519* (2013.01); *A61K 9/0095* (2013.01); *A61K 9/14* (2013.01); *A61K 9/48* (2013.01); *A61K 47/12* (2013.01); *A61K 47/20* (2013.01); *A61K 47/26* (2013.01); *A61K 47/38* (2013.01)

(58) Field of Classification Search
CPC ...... A61K 31/519; A61K 9/0095; A61K 9/14; A61K 9/48; A61K 47/12; A61K 47/20; A61K 47/26
See application file for complete search history.

(56) References Cited

U.S. PATENT DOCUMENTS

| 4,724,141 | A  | 2/1988  | Schmidt et al. |
| 6,074,670 | A  | 6/2000  | Stamm et al. |
| 8,772,283 | B2 | 7/2014  | Nakamura |
| 9,108,973 | B2 | 8/2015  | Sagara et al. |
| 9,241,908 | B2 | 1/2016  | Khedkar et al. |
| 9,532,990 | B2 | 1/2017  | He |
| 9,725,723 | B2 | 8/2017  | Hedjarn et al. |
| 9,861,636 | B2 | 1/2018  | He |
| 10,124,003 | B2 | 11/2018 | Sootome |
| 10,300,066 | B2 | 5/2019  | Fürstner |
| 10,350,214 | B2 | 7/2019  | Tomimatsu et al. |
| 10,434,103 | B2 | 10/2019 | Egami |
| 2002/0168413 | A1 | 11/2002 | Stamm et al. |
| 2004/0102360 | A1 | 5/2004  | Barnett et al. |
| 2006/0110383 | A1 | 5/2006  | Honjo |
| 2007/0254033 | A1 | 11/2007 | Bhatt et al. |
| 2007/0299075 | A1 | 12/2007 | Bhide et al. |
| 2008/0026057 | A1 | 1/2008  | Benke |
| 2008/0207665 | A1* | 8/2008 | Hashizume et al. ... A61K 31/46 514/278 |
| 2010/0048620 | A1 | 2/2010  | Yamamoto |
| 2010/0285143 | A1 | 11/2010 | Khedkar et al. |
| 2011/0053866 | A1* | 3/2011 | Duffield et al. ........ A61K 38/16 514/21.2 |
| 2012/0101064 | A1 | 4/2012  | Howard |
| 2013/0061403 | A1 | 3/2013  | Bringewatt |
| 2013/0158000 | A1 | 6/2013  | Brohm |
| 2013/0190354 | A1 | 7/2013  | Wen et al. |
| 2014/0005185 | A1 | 1/2014  | Nakamura |

(Continued)

FOREIGN PATENT DOCUMENTS

| AU | 2018448845 A1 | 6/2021 |
| AU | 2020228514 A1 | 10/2021 |

(Continued)

OTHER PUBLICATIONS

Xiaorong He, et al, Development of a rapidly dispersing tablet of a poorly wettable compound-formulation DOE and mechanistic study of effect of formulation excipients on wetting of celecoxib, International Journal of Pharmaceutics, vol. 353, Issues 1-2, 2008, pp. 176-186, ISSN 0378-5173 (Year: 2008).*

Bathool A, Gowda DV, Khan MS, Ahmed A, Vasudha SL, Rohitash K. Development and evaluation of microporous osmotic tablets of diltiazem hydrochloride. J Adv Pharm Technol Res. Apr. 2012;3(2):124-9. doi: 10.4103/2231-4040.97292. (Year: 2012).*

Fozia Israr, et al, Formulation design and evaluation of Cefuroxime axetil 125 mg immediate release tablets using different concentration of sodium lauryl sulphate as solubility enhancer. Brazilian Journal of Pharmaceutical Sciences, vol. 50, n. 4, Oct./Dec. 2014 (Year: 2014).*

(Continued)

*Primary Examiner* — Theodore R. Howell
(74) *Attorney, Agent, or Firm* — Rothwell, Figg, Ernst & Manbeck, P.C.

(57) ABSTRACT

The object of the present invention is to improve the dissolution and the absorption of (S)-1-(3-(4-amino-3-((3,5-dimethoxyphenyl)ethynyl-1H-pyrazolo[3,4-d]pyrimidin-1-yl-1-pyrrolidinyl)-2-propen-1-one effective as an antitumor agent from a pharmaceutical formulation comprising the same. Provided is a pharmaceutical composition comprising (S)-1-(3-(4-amino-3-((3,5-dimethoxyphenyl)ethynyl-1H-pyrazolo[3,4-d]pyrimidin-1-yl-1-pyrrolidinyl)-2-propen-1-one in combination with sodium alkyl sulfate having an alkyl group containing 10 to 18 carbon atoms, in particular, with sodium lauryl sulfate.

10 Claims, 1 Drawing Sheet

(56) References Cited

U.S. PATENT DOCUMENTS

| | | |
|---|---|---|
| 2014/0343035 A1 | 2/2014 | Dawson et al. |
| 2015/0031676 A1 | 1/2015 | Lobell |
| 2015/0164909 A1 | 6/2015 | Ichikawa |
| 2015/0166544 A1 | 6/2015 | Zhang |
| 2015/0307886 A1 | 10/2015 | Hedjtarn et al. |
| 2016/0102366 A1 | 4/2016 | Abe |
| 2016/0136168 A1* | 5/2016 | Sootome ............ A61K 31/519 |
| 2016/0193210 A1 | 7/2016 | Ochiiwa et al. |
| 2016/0200730 A1 | 7/2016 | He |
| 2016/0287699 A1 | 10/2016 | Karkera |
| 2017/0017516 A1* | 2/2017 | Vaslin-Chessex et al. .................. C12Q 1/68 |
| 2017/0035773 A1 | 2/2017 | Tomimatsu et al. |
| 2017/0065594 A1 | 3/2017 | He |
| 2017/0112894 A1 | 4/2017 | Kawabe |
| 2017/0209574 A1 | 7/2017 | Cao et al. |
| 2017/0252317 A1 | 9/2017 | Lyssikatos |
| 2018/0030067 A1 | 2/2018 | Hashimoto |
| 2018/0110782 A1 | 4/2018 | Egami |
| 2018/0177788 A1 | 6/2018 | Pachter |
| 2018/0207161 A1 | 7/2018 | He |
| 2019/0015417 A1 | 1/2019 | Sootome |
| 2019/0183897 A1 | 6/2019 | Ochiiwa et al. |
| 2020/0038407 A1 | 2/2020 | Tomimatsu et al. |

FOREIGN PATENT DOCUMENTS

| | | |
|---|---|---|
| AU | 2020229714 A1 | 10/2021 |
| CN | 105859721 A | 8/2016 |
| EA | 200970932 B1 | 4/2010 |
| EA | 201101566 A1 | 4/2010 |
| EP | 3424505 A1 | 1/2019 |
| EP | 3882248 A1 | 9/2021 |
| EP | 3888643 A1 | 10/2021 |
| JP | S61-068431 A | 4/1986 |
| JP | H11-005735 A | 1/1999 |
| JP | 2009-143967 A | 7/2009 |
| JP | 2011511759 A | 4/2011 |
| JP | 2011-524888 A | 9/2011 |
| JP | 2013079267 A | 5/2013 |
| JP | 2015-500307 A | 1/2015 |
| JP | 2015-508087 A | 3/2015 |
| JP | 2016-501520 A | 1/2016 |
| JP | 2016-104762 A | 6/2016 |
| JP | 2017-518276 A | 7/2017 |
| JP | 2018-002662 A | 1/2018 |
| JP | 2018-511611 A | 4/2018 |
| JP | 2018-519327 A | 7/2018 |
| JP | 2018-537420 A | 12/2018 |
| KR | 10-2009-0108100 A | 10/2009 |
| RU | 2173157 C2 | 9/2001 |
| RU | 2009127883 A | 1/2011 |
| RU | 2428421 C2 | 9/2011 |
| RU | 2493850 C2 | 9/2013 |
| RU | 2595866 C2 | 8/2016 |
| WO | 02/06213 A2 | 1/2002 |
| WO | 03/077914 A1 | 9/2003 |
| WO | 2004004771 | 1/2004 |
| WO | 2005/051906 A2 | 6/2005 |
| WO | 2005/121142 A1 | 12/2005 |
| WO | 2006/045514 A1 | 5/2006 |
| WO | 2007/014011 A2 | 2/2007 |
| WO | 2007/044515 A1 | 4/2007 |
| WO | 2007041712 A1 | 4/2007 |
| WO | 2007/087395 A2 | 8/2007 |
| WO | 2007127630 A1 | 11/2007 |
| WO | 2008/077557 A1 | 7/2008 |
| WO | 2008/121742 A2 | 10/2008 |
| WO | 2008/124161 A1 | 10/2008 |
| WO | 2009/153592 A1 | 12/2009 |
| WO | 2010/043865 A1 | 4/2010 |
| WO | 2011/093672 A2 | 8/2011 |
| WO | 2011115937 A1 | 9/2011 |
| WO | 2011/153514 A2 | 12/2011 |
| WO | 2012/137870 A1 | 10/2012 |
| WO | 2013/108809 A1 | 7/2013 |
| WO | 2013116293 A1 | 8/2013 |
| WO | 2014/007217 A1 | 1/2014 |
| WO | 2014/138364 A2 | 9/2014 |
| WO | 2014/172644 A2 | 10/2014 |
| WO | 2014/203959 A1 | 12/2014 |
| WO | 2015/008839 A1 | 1/2015 |
| WO | 2015/008844 A1 | 1/2015 |
| WO | 2016/136928 A1 | 9/2015 |
| WO | 2015/150900 A2 | 10/2015 |
| WO | 2016/115356 A1 | 7/2016 |
| WO | 2016/130917 A1 | 8/2016 |
| WO | 2016125169 A1 | 8/2016 |
| WO | 2016/161239 | 10/2016 |
| WO | 2016159327 A1 | 10/2016 |
| WO | 2017013160 A1 | 1/2017 |
| WO | 2017/086332 A1 | 5/2017 |
| WO | 2017150725 A1 | 9/2017 |
| WO | 2018130928 A1 | 7/2018 |
| WO | 2020/095452 A1 | 5/2020 |
| WO | 2020/096042 A1 | 5/2020 |
| WO | 2020/096050 A1 | 5/2020 |
| WO | 2020/110974 A1 | 6/2020 |
| WO | 2020/170355 A1 | 8/2020 |
| WO | 2020/171113 A1 | 8/2020 |
| WO | 2020/175697 A1 | 9/2020 |
| WO | 2020/175704 A1 | 9/2020 |
| WO | 2020/256096 A1 | 12/2020 |

OTHER PUBLICATIONS

Shaabani et al., "A patent review on PD-1/PD-L1 antagonists: small molecules, peptides and macrocycles (2015-2018)", EXpert Opin Ther Pat. 2018, 28(9), 665-678.

Tol et al., "Chemotherapy, Bevacizumab, and Cetuximab in Metastatic Colorectal Cancer", The New England Journal of Medicine, 2009; 360: 563-72.

Yu et al., "A phase ½ trial of ruxolitinib and erlotinib in patients with EGFR-mutant lung adenocarcinomas with acquired resistance to erlotinib", J Thorac Oncol. 2017, 12(1): 102-109.

Official Action dated Apr. 4, 2022 for RU Pat. Appln. 2021128137, 21 pages (Translation).

Kharkevich, Pharmacology: textbook, 10th ed., 2010, pp. 72-82 (Translation).

Urmancheeva et al., Modern hormone therapy of endometrial cancer, Siberian Oncological Journal, 2007, Appendix, pp. 89-93 (Translation).

Chissov et al., Oncology: textbook with CD, GEOTAR-Media, 2007. pp. 106-107 (Translation).

Tarutinov V.I. et al., Hormone therapy for breast cancer: the current state of the problem. // Oncology. vol. 9, 2, 2007, pp. 125-128 (Translation).

Kaprin A.D. et al., The role of hormone therapy in the complex treatment of localized and locally advanced prostate cancer // Russian Medical Journal, 28, 2006 (Translation).

Office Action dated Feb. 28, 2022 for RU Pat. Appln. No. 2021118562, 42 pages (Translation).

Ochiiwa, H., et al., "Abstract A270: TAS-120, a highly potent and selective irreversible FGFR inhibitor, is effective in tumors harboring various FGFR gene abnormalities", Molecular Cancer Therapeutics, vol. 12, No. 11_Supplement, 2013, p. A270, 5 pages.

Balko, J., et al., "Discordant Cellular Response to Presurgical Letrozole in Bilateral Synchronous ER+ Breast Cancers with a KRAS Mutation or FGFR1 Gene Amplification", Molecular Cancer Therapeutics, vol. 11, No. 10, 2012, 8 pages.

EESR dated Jul. 22, 2022 for EP patent application No. 19888521.2, 9 pages.

Official Action for RU Patent Application No. 2020133810 dated Feb. 16, 2021, 20 pages.

Qiang D. et al. Evaluation of the impact of sodium lauryl sulfate source variability on solid oral dosage form development // Drug development and industrial pharmacy.—2010.—vol. 36.—No. 12.—

(56) References Cited

OTHER PUBLICATIONS p. 1486-1496, Jun. 14, 2010, URL: https://www.tandfonline.com/doi/abs/1 0.3109/03639045.2010.488647, Abstract.

Hernandez et al., "Prospective Study of FGFR3 Mutations as a Prognostic Factor in Nonmuscle invasive Urothelial Bladder Carcinomas", Journal of Clinical Oncology, 2006, vol. 24, No. 22, pp. 3664-3671.

Gelsi-Boyer et al., "Comprehensive Profiling of 8p11-12 Amplification in Breast Cancer", Molecular Cancer Research, 2005, vol. 3, No. 12, pp. 655-667.

Turner et al., "FGFR1 Amplification Drives Endocrine Therapy Resistance and is a Therapeutic Target in Breast Cancer", Cancer Research, 2010, vol. 70, No. 5, pp. 2085-2094.

Elsheikh et al., "FGFR1 amplification in breast carcinomas: a chromogenic in situ hybridization analysis", Breast Cancer Research, 2007, vol. 9, No. 2, R23.

Corn et al., "Targeting Fibroblast Growth Factor Pathways in Prostate Cancer", Clin. Cancer Res., 2013, 19(21), pp. 5856-5866.

Boget et al., "Fibroblast growth factor receptor 1 (FGFR1) is over-expressed in benign prostatic hyperplasia whereas FGFR2-IIIc and FGFR3 are not", European Journal of Endocrinology, 2001, 145, pp. 303-310.

Formisano et al., "Association of FGFR1 with Eralpha Maintains ligand-Independent ER Transcription and Mediates Resistance to Estrogen Deprivation in ER+ Breast Cancer", Clinical Cancer Research, 2017, vol. 23, Issue 20, pp. 6138-6150.

Bluemn et al., "Androgen Receptor Pathway-Independent Prostate Cancer is Sustained through FGF Signaling", Cancer Cell, 2017, 32, pp. 474-489.

Musolino et al., "Phase II, randomized placebo-controlled study of dovitinib in combination with fulvestrant in postmenopausal patients with HR+, HER2-breast cancer that had progressed during or after prior endocrine therapy", Breast Cancer Research, 2017, vol. 19, Art. No. 18, pp. 1-14.

Perez-Garcia et al., "Targeting FGFR pathway in breast cancer", The Breast, 2018, vol. 37, pp. 126-133.

Sobhani et al., "Current Status of Fibroblast Growth Factor Receptor-Targeted Therapies in Breast Cancer", cells. 2018, vol. 7, Issue 7, Art. No. 76, pp. 1-14.

Andre, "Rationale for targeting fibroblast growth factor receptor signaling in breast cancer", Breast Cancer Research and Treatment, 2015, vol. 150, Issue 1, pp. 1-8.

Xie et al., "FGFR2 Gene Amplification in Gastric Cancer Predicts Sensitivity to the Selective FGFR Inhibitor AZD4547", Clinical Cancer Research, vol. 19, No. 9, pp. 2572-2583 (2013).

Byron et al., "Fibroblast Growth Factor Receptor Inhibition Synergizes with Paclitaxel and Doxorubicin in Endometrial Cancer Cells" International Journal of Gynecological Cancer, vol. 22, No. 9, pp. 1517-1526 (2012).

Wilson et al., "Widespread potential for growth-factor-driven resistance to anticancer kinase inhibitors", Nature, 2012, 487(7408): 505-509.

Chang et al., "Multiple receptor tyrosine kinase activation attenuates therapeutic efficacy of the fibroblast growth factor receptor 2 inhibitor AZD4547 in FGFR2 amplified gastric cancer", Oncotarget, vol. 6, No. 4, 2014, pp. 2009-2022.

Kleespies et al., "Tyrosine kinase inhibitors and gemcitabine: New treatment options in pancreatic cancer?", Drug Resistance Updates, 2006, pp. 1-18.

Decision of Refusal for JP patent application No. 2017-149671, dated May 15, 2018, 3 pages (Translation).

Seiichiro Hikime, Lectures of Experimental Chemistry (continued) 2 Separation and purification, 1967, pp. 159-162, 184-193.

Handbook of Solvents, 1985, pp. 47-51.

Version 4 Lectures on experimental chemistry 1 Basic operation I, 1990, pp. 184-189.

Impurities: Guideline for Residual Solvents, 1998, No. 307, pp. 1-11.

Office Action for RU patent application No. 2016105133, dated Feb. 27, 2018, 3 pages (Translation).

Falkman, "Angiogenesis in cancer, vascular, rheumatoid and other disease", Nature Medicine, 1995, vol. 1, No. 1, pp. 27-31.

Lieu et al., "Beyond VEGF: Inhibition of the fibroblast growth factor pathway and antiangiogenesis", Clinical Cancer Research, 2011, vol. 17, No. 19, pp. 6130-6139.

ISR for PCT/JP2013/050740, dated Apr. 16, 2013, 3 pages (Translation).

Gong et al., "A novel 3-arylethynyl-substituted pyrido[2,3-b]pyrazine derivatives and pharmacophore model as Wnt2/β-catenin pathway inhibitors in non-small-cell lung cancer cell lines", Bioorganic &Medicinal Chemistry, vol. 19, 2011, pp. 5639-5647.

Office Action for the JP patent application No. 2016-566309, dated Feb. 2, 2017, 3 pages (Translation).

Byrn et al., "Pharmaceutical Solids: A Strategic Approach to Regulatory Considerations", Pharmaceutical Research, 1995, 12(7), pp. 945-954.

Sootome et al., "Identification and Biological Characterization of a Highly Potent, Irreversible Inhibitor of FGFR, TAS-2985", European Journal of Cancer, 48:116, 2012.

Nakatsuru et al., "Significant in Vivo Antitumor Activity by a Highly Potent, Irreversible FGFR Inhibitor, TAS-2985", European Journal of Cancer, 2012, vol. 48, Suppl. 6, pp. 117.

Gangjee et al., "Synthesis of 5,7-disubstituted-4-methyl-7H-pyrrolo[2,3-d]pyrimidin-2-amines as microtubule inhibitors", Bioorganic & Medicinal Chemistry, 2013, 3, vol. 21, No. 5, pp. 1180-1189.

Fukumoto et al., "FGF23 is a hormone-regulating phosphate metabolism—Unique biological characteristics of FGF23", Bone, 2007, vol. 40, pp. 1190-1195.

Shimada et al., "Targeted ablation of Fgf23 demonstrates an essential physiological role of FGF23 in phosphate and vitamin D metabolism", Journal of Clinical Investigation, 2004, vol. 113, No. 4, pp. 561-568.

Razzaque et al., "FGF-23, vitamin D and calcification: the unholy triad", Nephrol. Dial. Transplant., 2005, vol. 20, pp. 2032-2035.

Jonker et al., Annals of Oncology 22: pp. 1413-1419, 2011.

Pharmacodia (http://en.pharmacodia.com/web/drug/1_1258.html , retrieved Jun. 10, 2017), 2 pages.

Cayman (https://www.caymanchem.com/product/21136 , retrieved Jun. 10, 2017), 4 pages.

Konecny et al., "Activity of the Fibroblast Growth Factor Receptor Inhibitors Dovitinib (TKI258) and NVP-BGJ398 in Human Endometrial Cancer Cells", Molecular Cancer Therapeutics 12(5); 632-642, 2013.

Caira M R, "Crystalline Polymorphism of Organic Compounds", Topics in Current Chemistry, 1998, pp. 163-208.

Office Action dated Feb. 5, 2019 for MX patent application No. MX/a/2017/012568, 9 pages.

Byron et al., "The N550K/H Mutations in FGFR2 Confer Differential Resistance to PD173074, Dovitinib, and Ponatinib ATP-Competitive Inhibitors", Neoglasia, vol. 15, pp. 975-988, 2013.

Office Action dated Jun. 26, 2019 for U.S. Appl. No. 16/149,522.

Kubinyi, "3D QSAR in Drug Design: Ligand-Protein interactions and Molecular Similarity", vol. 2-3, 1998, pp. 243-244.

Singh et al., "Transforming Fusions of FGFR and TACC Genes in Human Glioblastoma", Science, 2012, vol. 337, pp. 1231-1235.

Patani et al., "Landscape of activating cancer mutations in FGFR kinases and their differential responses to inhibitors in clinical use", Oncotarget, 2016, vol. 7, No. 17, pp. 24252-24268.

Borad et al. "Fibroblast growth factor receptor 2 fusions as a target for treating cholangiocarcinoma", Curr Opin Gastroenterol., 2015, vol. 31(3), pp. 264-268.

Official Action for RU Pat. Appln. No. 2018134777 dated Jun. 1, 2020, 10 pages (Translation).

Brown et al., "Maximizing the potential of AKT inhibitors as anti-cancer treatments", Pharmacology & Therageutics, 2017, vol. 172, pp. 101-115.

Yunokawa et al., "First-in-human phase I study of TAS-117, an allosteric AKT inhibitor, in patients with advanced solid tumours", Annals of Oncology, 2019, vol. 30, Suppel. 5, p. v169.

Bavin et al., "Polymorphism in Process Development", Chemistry & Industry, 1989, (16), pp. 527-529.

Belikov V.G., Pharmaceutical Chemistry in Two Parts, "Pharmaceutical Chemistry", 1993, 432 pp. 43-47.

(56) References Cited

OTHER PUBLICATIONS

Mashkovsky M.D., Medicines.—16th ed., Revised—M .: Novaya Volna, 2012.—1216 p.

Mashkovsky M.D. Medicines, Moscow, New Wave, 2001, in 2 parts, vol. 1, p. 11.

Official Action for RU Pat. Appln. No. 2018134777 dated Apr. 28, 2021, 10 pages (Translation).

Manning et al., "AKT/PKB Signaling: Navigating Downstream", Cell, 2007, 129, pp. 1261-1274.

Markman et al., "Status of PI3K inhibition and biomarker development in cancer therapeutics", Annals of Oncology 2010, 21: pp. 683-691.

Yap et al., "First-in-Man Clinical Trial of the Oral Pan-AKT Inhibitor MK-2206 in Patients With Advanced Solid Tumors", Journal of Clinical Oncology, 2011, vol. 29, No. 35, pp. 4688-4695.

Saleh et al., "Abstract LB-197: First-in-human study with ARQ 092, a novel pan AKT-inhibitor: Results from the advanced solid tumors cohorts.", 2013, 73 (Suppl 8).

Banerji et al., "A Phase 1 open-label study to identify a dosing regimen of the pan-AKT inhibitor AZD5363 for evaluation in solid tumors and in PIK3CA-mutated breast and gynecologic cancers", 2018, (9): 2050-2059, (doi: 10.1158/1078/0432. CRC-17-2260).

Abe et al., "Characterization of TAS-117, a novel, highly potent and selective inhibitor of AKT", 2017, Poster of EORTC-NCI-AACR 2017, 1 page.

Jones et al., "Recurrent somatic alterations of FGFR1 and NTRK2 in pilocytic astrocytoma", Nature Genetics, 2013, vol. 45, No. 8, pp. 927-932.

Pardoll, "The blockade of immune checkpoints in cancer immunotherapy", Nature Review Cancer, 2012, vol. 12, pp. 252-264.

Topalian et al., "Safety, Activity, and Immune Correlates of Anti-PD-1 Antibody in Cancer", New England Journal of Medicine, 2012, vol. 366, No. 26, pp. 2443-2454.

Sharma et al., "Primary, Adaptive, and Acquired Resistance to Cancer immunotheragy", Cell, 2017, vol. 168, pp. 707-723.

Zaretsky et al., "Mutations Associated with Acquired Resistance to PD-1 Blockade in Melanoma", New England Journal of Medicine, 2016, vol. 375, No. 9, pp. 819-829.

Arlauckas et al., "In vivo imaging reveals a tumor-associated macrophage-mediated resistance pathway in anti-PD-1 therapy", Science Translational Medicine, 2017, vol. 9, eeal3604.

Nassar et al., "Sequential Response to FGFR3 Inhibition With Subsequent Exceptional Response to Atezolizumab in a Patient With FGFR3-TACC3 F ion-Positive Metastatic Urothelial Carcinoma", JCO Precision Oncology, 2018, (DOI:10. 1200/P0. 18. 00117.

Liu et al., "Reductions in Myeloid-Derived Suppressor Cells and Lung Metastases using AZD4547 Treatment of a Metastatic Murine Breast Tumor Model", Cellular Physiology and Biochemistry, 2014, vol. 33, pp. 633-645.

Weber et al., "Myeloid-Derived Suppressor Cells Hinder the Anti-Cancer Activity of immune Checkpoint inhibitors", Frontier in Immunology, 2018, vol. 9, Article 1310. doi:10. 3389/fimmu. 2018. 01310.

Wang et al. "Drug-excipient interactions resulting from powder mixing. V. Role of sodium lauryl sulfate", vol. 60, No. 1, 1990, pp. 61-78.

Extended European search report dated Nov. 11, 2021 for EP Pat. Appln. 19771998.2.

Written Opinion of ISA for PCT/JP2013/050740, dated Jun. 16, 2013, 6 pages (Translation).

ISR for PCT/JP2014/069105, dated Sep. 2, 2014, 4 pages.

Written Opinion of ISA for PCT/JP2014/069105, dated Sep. 2, 2014, 7 pages (Translation).

ISR for PCT/JP2014/069086, dated Sep. 2, 2014, 3 pages.

Written Opinion of ISA for PCT/JP2014/069086, dated Sep. 2, 2014, 6 pages (translation).

ISR for PCT/JP2016/060844, dated Jun. 28, 2016, 2 pages.

Written Opinion of ISA for PCT/JP2016/060844, dated Jun. 28, 2016, 5 pages (Translation).

ISR for PCT/JP2017/008599, dated Apr. 4, 2017, 3 pages.

Written Opinion of ISA for PCT/JP2017/008599, dated Apr. 4, 2017, 10 pages (Translation).

ISR for PCT/JP2018/041744, dated Jan. 8, 2019, 1 page.

Written Opinion of ISA for PCT/JP2018/041744, dated Jan. 8, 2019, 6 pages (Translation).

ISR for PCT/JP2019/045901, dated Feb. 18, 2020, 3 pages.

Written Opinion of ISA for PCT/JP2019/045901, dated Feb. 18, 2020, 6 pages (Translation).

ISR for PCT/JP2019/043926, dated Dec. 24, 2019, 2 pages.

Written Opinion of ISA for PCT/JP2019/043926, dated Dec. 24, 2019, 5 pages (Translation).

ISR for PCT/JP2019/006265, dated May 28, 2019, 2 pages.

Written Opinion of ISA for PCT/JP2019/006265, dated May 28, 2019, 6 pages (Translation).

ISR for PCT/JP2020/008509, dated Apr. 14, 2020, 2 pages.

Written Opinion of ISA for PCT/JP2020/008509, dated Apr. 14, 2020, 5 pages (Translation).

ISR for PCT/JP2020/024113, dated Aug. 18, 2020, 3 pages.

Written Opinion of ISA for PCT/JP2020/024113, dated Aug. 18, 2020, 4 pages (Translation).

ISR for PCT/JP2019/011251, dated May 21, 2019, 2 pages.

Written Opinion of ISA for PCT/JP2019/011251, dated May 21, 2019, 6 pages (Translation).

ISR for PCT/JP2019/043857, dated Dec. 24, 2019, 2 pages.

Written Opinion of ISA for PCT/JP2019/043857, dated Dec. 24, 2019, 6 pages (Translation).

ISR for PCT/JP2020/006464, dated Mar. 24, 2020, 3 pages.

Written Opinion of ISA for PCT/JP2020/006464, dated Mar. 24, 2020, 4 pages (Translation).

ISR for PCT/JP2020/008527, dated Apr. 14, 2020, 2 pages.

Written Opinion for ISA for PCT/JP2020/08527, dated Apr. 14, 2020, 6 pages (Translation).

Request for the Submission of an Opinion dated Jan. 6, 2023 for KR Pat. Appln. No. 10-2022-7025906 (11 pages).

Katoh, Masaru; FGFR inhibitors: Effects on cancer cells, tumor microenvironment and whole-body homeostasis (Review), International Journal of Molecular Medicine, 2016, vol. 38, pp. 3-15.

Notice of Reasons for Refusal for the related JP Patent Application No. 2021-502667, dated Aug. 30, 2021, 9 pages.

Kalyukina et al., "TAS-120 Cancer Target Binding:Defining Reactivity and Revealing the First Fibroblast Growth Factor Receptor 1 (FGFR1) Irreversible Structure", ChemMedChem 14, 2019, 494-500.

Meric-Bernstam et al., "Efficacy of TAS-120 an irreversible fibroblast growth factor receptor (FGFR) inhibitor, in cholangiocarcinoma patients with FGFR pathway alternations who were previously treated with chemothrapy and other FGFR inhibitors", Annals of Oncology 29 (Supplement 5), 2018, v100-v110, 1 page.

Bockorny et al., "RAS-MAPK Reactivation Facilitates Acquired Resistance in FGFR1-Amplified Lung Cancer and Underlies a Rationale for Upfront FGFR-MEK Blockade", Molecular Cancer Therapeutics, 17(7), 2018, pp. 1526-1539.

Orinitz et al., "Achondroplasia: Development, Pathogenesis, and Therapy", Developmental Dynamics, 2017, 246 (4), 291-309.

Bellus et al., "Distinct Missense Mutations of the FGFR3 Lys650 Codon Modulate Receptor Kiniase Activation and the Severity of the Skeletal Dysplasia Phenotype", Am J Hum Genet., 2000, 67 (6), 1411-21.

Rousseau et al., "Mutations in the gene encoding fibroblast growth factor receptor-3 in achondroplasia", Nature, 1994, 371 (6494), 252-4.

Bellus et al., "A recurrent mutation in the tyrosine kinase domain of fibroblast growth factor receptor 3 causes hypochondroplasia", Nature Genetics, 1995, 10 (3), 357-9.

Bonaventure et al., "Common Mutations in the Fibroblast Growth Factor Receptor 3 (FGFR 3) Gene Account for Achondroplasia, Hypochondroplasia, annd Thanatophoric Dwarfism", American Journal of Medical Genetics, 1996, 63 (1), 148-54.

(56) References Cited

OTHER PUBLICATIONS

Komla-Ebri et al., "Tyrosine kinase inhibitor NVP-BGJ398 functionally improves FGFR3-related dwarfism in mouse model", J Clin Invest., 2016, vol. 126, No. 5, pp. 1871-1884.
Garcia et al., Postnatal soluble FGFR3 therapy rescues achondroplasia symptoms and restores bone growth in mice, Sci Transl Med., 2013, vol. 5, No. 203, Art. 203ra124.
Ramaswami et al., Genotype and phenotype in hypochondroplasia, J Pediatr, 1998, vol. 133, No. 1, pp. 99-102.
Kimura et al., The incidence of thanatophoric dysplasia mutations in FGFR3 gene is higher in low-grade or superficial bladder carcinomas, Cancer, 2001, vol. 92, No. 10, pp. 2555-2561.
ISR and Written Opinion of PCT/JP2021/003133, dated Mar. 16, 2021, 16, pages.
Lattanzi et al., "Current Status and Future Direction of Immunotherapy in Urothelial Carcinoma", Current Oncology Reports, vol. 21, No. 3, 2019, pp. 1-12.
EESR dated Nov. 4, 2022 for EP Patent Application No. 207632076 dated Nov. 4, 2022, 9 pages.
ISR and Written Opinion for PCT/JP2021/015032 dated May 11, 2021, , 11 pages.
Mashkovsky, "Medications", Moscow, "Medicine", 1993, part 1, p. 8., 3 pages.
Bastin et al, "Salt Selection and Optimisation Procedures for Pharmaceutical New Chemical Entities", Organic Process Reseach & Development, 2000, 4, pp. 427-435.
Vengerovsky AI, "Pharmacological incompatibility", Bulletin Siberian Medicine, 2003, pp. 49-56.
Office Action dated Feb. 7, 2023 for RU Pat. Appl. 2021128138, 32 pgs.
"Chemical Encyclopedic Dictionary", Soviet Encyclopedia, 1983, pp. 130-131, with translation.
Belikov V.G. "Pharmaceutical chemistry", 2007, MEDpress-inform, pp. 27-29, with translation.
Sergeev, "Short course of molecular pharmacology", 1975, p. 10, with translation.
Kholodov L.E. et al. "Clinical pharmacokinetics", Medicine, 1985, pp. 83-98, 134-138, 160, 378-380, with translation.
Wesserling et al., "Will In Vitro Tests Replace Animal Models in Experimental Oncology", Journal of tissue science and engineering, 2011, V.2, No. 1, 102e, Abstract.
Szajewska, "Evidence-based medicine and clinical research: both are needed, neither is perfect", Annals of nutrition and metabolism, 2018, V.72, N.3, pp. 13-23.
OA dated Apr. 13, 2023 for RU Pat. Appl. 2021118562, 23 pgs.
Harris, "TAS-117 shows Limited Efficacy in Ovarian, Breast Tumors", 2021, Retrieved from the internet: https://www.onclive.com/view/tas-117-shows-limited-efficacy-in-ovarian-breast-tumors, 3 pages.
Lee et al., "Phase 2 study of TAS-117, an allosteric akt inhibitor in advanced solid tumors harboring phosphatidylinositol 3-kinase/v-akt murine thymoma viral oncogene homolog gene mutations", Investigational New Drugs, 2021, vol. 39, No. 5, pp. 1366-1374.
EESR dated Jun. 1, 2023 for EP Pat. Appln. No. 20827927.3, 13 pages.
Shim et al., "One target, different effects: a comparison of distinct therapeutic antibodies against the same targets", Experimental and Molecular Medicine, vol. 43, No. 10, 539-549, Oct. 2011.
Russian Office Action issued in Application No. 2021128137/10 dated Jun. 29, 2023, 13 pgs.
Jain et al., "Effect of pH-Sodium Lauryl Sulfate Combination on Solubillzation of PG-300995 (an Anti-HIV Agent): A Technical Note". AAPS Pharma Sci Tech, 2004, 5(3), pp. 1-3.
Hearing Notice dated Oct. 12, 2023 for IN Pat. Appln. No. 202017041678 (2 pages).
Office Action dated Sep. 19, 2023 for RU Pat. Appln. No. 2022101214, 13 pgs.

* cited by examiner

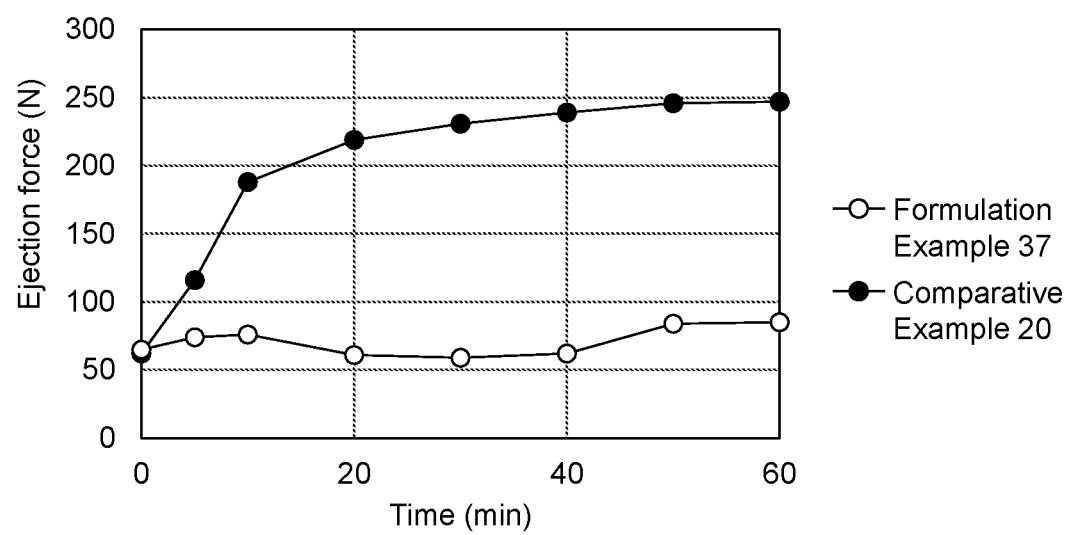

PHARMACEUTICAL COMPOSITION INCLUDING SODIUM ALKYL SULFATE

This application is a 35 U.S.C. 371 National Phase Entry Application from PCT/JP2019/011251, filed Mar. 18, 2019, which claims the benefit of Japanese Patent Application No. 2018-051620 filed on Mar. 19, 2018, the disclosure of which is incorporated herein in its entirety by reference.

TECHNICAL FIELD

The present invention relates to a pharmaceutical composition comprising (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof and sodium alkyl sulfate, in particular, the pharmaceutical composition for oral administration.

BACKGROUND ART

Bioavailability is an indicator showing the level of an administered drug to reach in blood circulating throughout the body and to act thereon, and a clinically important parameter that is closely associated with medicinal effects and toxicity. In general, a drug having low bioavailability may not provide expected medicinal effects, or due to large fluctuations in one individual or between individuals, it may be difficult to predict and/or control medicinal effects and toxicity. Accordingly, in the development of drug products, it is important to obtain appropriate drug bioavailability. In the case of a drug for oral administration, the drug is affected by absorption ratio from intestinal tract and the metabolism in the liver and/or intestinal tract. In particular, in the case of a poorly water-soluble drug, it becomes important to improve the drug dissolution from a formulation or the drug solubility in water to obtain appropriate bioavailability.

As way for improving the dissolution or absorption of a drug, the particle size reduction or solubilization of a drug substance, and a method of mixing a solubilizer such as a surfactant with a drug substance have been generally known. However, preferable surfactants are different depending on the structure and properties of an active ingredient and the type of the formulation, and it is not easy to find an optimal formulation for a poorly water-soluble drug.

It has been known that sodium lauryl sulfate, one of anionic surfactants, can be included in a pharmaceutical formulation, as a stabilizer, a surfactant, a lubricant, a solubilizer, a base, a binder, a brightener, an excipient, a disintegrant, an emulsifier, a foaming agent, a dispersant, or the like. For example, it was reported that sodium lauryl sulfate was added to granules containing a specific compound as a solubilizing agent to prepare a pharmaceutical formulation (Patent Literature 1).

On the other hand, as a compound having excellent FGFR inhibitory action and exhibiting antitumor activity, (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one (hereinafter also referred to as "Compound A") has been reported (Patent Literatures 2 to 6).

Regarding Compound A, neither the improvement of the dissolution thereof, nor the combined use of Compound A with sodium alkyl sulfate for other purposes has been reported.

CITATION LIST

Patent Literature

Patent Literature 1: JP Patent Publication (Kokai) No. 2016-104762 A

Patent Literature 2: International Publication No. WO2013/108809

Patent Literature 3: International Publication No. WO2015/008844

Patent Literature 4: International Publication No. WO2015/008839

Patent Literature 5: International Publication No. WO2016/159327

Patent Literature 6: International Publication No. WO2017/150725

SUMMARY OF INVENTION

Technical Problem

While Compound A has excellent FGFR inhibitory action and antitumor activity, there was room for improvement in ensuring appropriate bioavailability when formulated. For example, improvement of the dissolution in a neutral pH range and the absorption of Compound A has been required. Accordingly, it is an object of the present invention to provide a pharmaceutical composition comprising Compound A or a pharmaceutically acceptable salt thereof, having more excellent dissolution, stability, and absorption, and being easily produced.

Solution to Problem

The present inventors have added various compounds into a composition comprising Compound A or a pharmaceutically acceptable salt thereof, and conducted various studies regarding the presence or absence of the effect of improving dissolution, stability and absorption of Compound A. As a result, it was found that, by adding sodium alkyl sulfate to Compound A or a pharmaceutically acceptable salt thereof, a pharmaceutical composition having excellent dissolution, stability and absorption and also excellent manufacturability can be obtained. The present inventors have further conducted studies to find more effective excipients to be used in the pharmaceutical composition comprising Compound A or a pharmaceutically acceptable salt thereof and sodium alkyl sulfate, thereby achieving the present invention.

Specifically, the present invention relates to the following [1] to [15].

[1] A pharmaceutical composition comprising (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one having the following structure, or a pharmaceutically acceptable salt thereof, and sodium lauryl sulfate:

(Compound A)

[Formula 1]

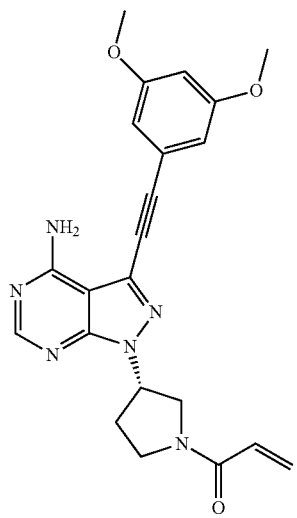

[2] The composition according to [1] above, comprising sodium lauryl sulfate in a range of 0.05 to 15 parts by mass, relative to 1 part by mass of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one.

[3] The composition according to [1] or [2] above, comprising sodium lauryl sulfate in a range of 0.2 to 5 parts by mass, relative to 1 part by mass of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one.

[4] The composition according to any one of [1] to [3] above, further comprising at least one compound selected from the group consisting of crospovidone, carmellose sodium, and carmellose calcium.

[5] The composition according to [4] above, comprising crospovidone.

[6] The composition according to any one of [1] to [5] above, comprising sodium lauryl sulfate in a range of 0.2 to 5 parts by mass, and further comprising crospovidone in a range of 0.2 to 5 parts by mass, relative to 1 part by mass of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one.

[7] The composition according to any one of [1] to [6] above, further comprising at least one compound selected from the group consisting of D-mannitol and lactose.

[8] The composition according to any one of [1] to [7] above, in the form of syrup, a powder, a granule, a tablet, or a capsule.

[9] A method for improving the dissolution of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one from a pharmaceutical composition comprising (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof, wherein the method comprises adding sodium lauryl sulfate to the pharmaceutical composition.

[10] A method for improving the absorption of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one, wherein the method comprises adding sodium lauryl sulfate to a pharmaceutical composition comprising (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof.

[11] A method for improving the manufacturability of a pharmaceutical composition comprising (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof, wherein the method comprises adding sodium lauryl sulfate to the pharmaceutical composition.

[12] Use of sodium lauryl sulfate for improving the dissolution of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof.

[13] Use of sodium lauryl sulfate for improving the absorption of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof.

[14] Use of sodium lauryl sulfate for improving the manufacturability of a pharmaceutical composition comprising (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof.

[15] Use of sodium lauryl sulfate for producing a pharmaceutical composition comprising (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof.

The present description includes the content disclosed in Japanese Patent Application No. 2018-051620, from which the present application claims priority.

Advantageous Effects of Invention

The present invention can provide a pharmaceutical composition comprising Compound A or a pharmaceutically acceptable salt thereof and sodium alkyl sulfate, which has excellent dissolution, stability and absorption, and is also excellent in terms of manufacturability such as lubricative property and flowability.

BRIEF DESCRIPTION OF DRAWINGS

FIG. 1 FIG. 1 shows the results of evaluation of the ejection force required when the tablets of Formulation Example 37 and Comparative Example 20 are discharged from a tableting machine.

DESCRIPTION OF EMBODIMENTS

The pharmaceutical composition of the present invention comprises, as an active ingredient, Compound A or a pharmaceutically acceptable salt thereof. The pharmaceutical composition of the present invention may also comprise other active ingredients, as long as it exhibits the effects of the present invention. The structure of Compound A ((S)-1-(3-(4-amino-3-((3,5-dimethoxyphenyl)ethynyl)-1H-pyrazolo[3,4-d]pyrimidin-1-yl)-1-pyrrolidinyl)-2-propen-1-one) is shown below.

(Compound A)

[Formula 2]

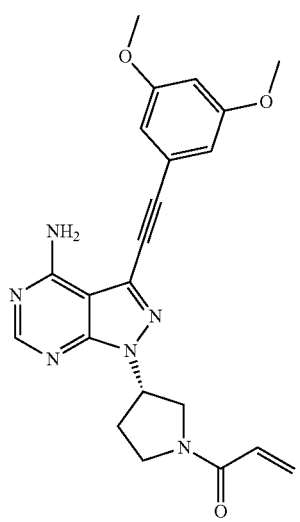

Compound A or a pharmaceutically acceptable salt thereof may be solvated (for example, hydrated) or unsolvated. In the present invention, both of solvated and unsolvated forms are included in "Compound A or a pharmaceutically acceptable salt thereof." The pharmaceutically acceptable salt of Compound A is not particularly limited, and examples thereof may include: addition salts with inorganic acids such as hydrochloric acid and sulfuric acid; addition salts with organic acids such as acetic acid, citric acid, tartaric acid and maleic acid; salts with alkali metals such as potassium and sodium; salts with alkaline earth metals such as calcium and magnesium; and salts with organic bases such as ammonium salts, ethylamine salts and arginine salts. Compound A or a pharmaceutically acceptable salt thereof can be produced, for example, by the method described in Patent Literature 2 or 5. In the present description, the term "Compound A" is intended to include the pharmaceutically acceptable "salt" of Compound A and the above-described "solvate."

From the viewpoint of dissolution, stability, absorption, manufacturability, etc., the amount of Compound A or a pharmaceutically acceptable salt thereof used in the present invention is preferably 1% to 50% by mass, more preferably 2% to 30% by mass, and further preferably 3% to 18% by mass, based on the total amount of the pharmaceutical composition.

In order to improve bioavailability of Compound A after administration, it is required to improve, in particular, the dissolution from the formulation in vivo, and the absorption into a body of Compound A.

As described above, a solubilizer may generally be used for a pharmaceutical composition comprising a poorly water-soluble active ingredient. Examples of solubilizers may include a surfactant, a polyether compound, and a poloxamer. Examples of surfactants may include alkyl sulfate, sucrose fatty acid ester (DK ester, etc.), polysolvate (Tween 20, Tween 60, Tween 80, etc.), and polyoxyethylene castor oil (Cremophor, Cremophor EL, etc.). Examples of polyether compounds may include polyethylene glycol (PEG400, PEG4000, PEG6000, Macrogol, etc.). The poloxamer may be, for example, Lutrol (Lutrol F68, etc.).

When sodium alkyl sulfate was used as a solubilizer, the solubility of Compound A could be significantly enhanced, in comparison to the use of other solubilizers. In addition, the use of sodium alkyl sulfate could not only maintain the chemical stability of Compound A and the physical stability of the dosage form of the pharmaceutical composition, but could also enhance the absorption of Compound A when administered orally.

Sodium alkyl sulfate may be, for example, those having an alkyl group containing 10 to 18 carbon atoms. Specific examples thereof may include sodium decyl sulfate, sodium lauryl sulfate (also referred to as "SLS" or "sodium dodecyl sulfate (SLS)"), sodium tetradecyl sulfate, sodium cetyl sulfate (sodium hexadecyl sulfate), and sodium stearyl sulfate (sodium octadecyl sulfate). From the viewpoint of dissolution, stability, absorption, manufacturability, etc., the sodium alkyl sulfate used in the present invention is preferably sodium lauryl sulfate. As sodium lauryl sulfate, NIKKOL SLS (manufactured by Nikko Chemicals Co., Ltd.), Emal OS (Kao Corporation), or Kolliphor SLS (BASF Corporation) can be obtained and suitably used.

From the same viewpoint as mentioned above, sodium alkyl sulfate can be used in a range of 0.01 to 25 parts by mass, relative to 1 part by mass of Compound A, preferably 0.05 to 15 parts by mass, more preferably 0.1 to 10 parts by mass, even more preferably 0.2 to 5 parts by mass, further preferably 0.25 to 3 parts by mass, still further preferably 0.75 to 1.5 parts by mass, and particularly preferably 1 part by mass, relative to 1 part by mass of Compound A. Moreover, sodium alkyl sulfate is preferably used in an amount of 1% to 50% by mass, based on the total amount of the pharmaceutical composition, and more preferably 2% to 30% by mass, even more preferably 3% to 18% by mass, further preferably 4% to 12% by mass, and particularly preferably 4% to 5% by mass, 6% to 7% by mass, or 9% to 10% by mass, based on the total amount of the pharmaceutical composition.

The term "dissolution" used herein means the dissolution of Compound A from a composition comprising Compound A (a pharmaceutical formulation). The dissolution can be examined according to the dissolution test method (paddle method) of the Japanese Pharmacopoeia 16th Edition. The improvement of the dissolution can be judged with a reduction in the disintegration time, or the dissolution ratio when an equilibrium state is achieved. By improving the dissolution of Compound A from a pharmaceutical formulation, the medicinal effects of Compound A as an active ingredient can be more appropriately exhibited.

The term "stability" used herein includes both the stability of a formulation including a pharmaceutical composition, and the chemical stability of Compound A. The improvement of stability can be judged by comparing the state of a pharmaceutical formulation before and after storage of the pharmaceutical formulation under the same conditions, and also by comparing the chemical purity of Compound A using high performance liquid chromatography or the like. Considering the storage and distribution of pharmaceutical products, the improvement of stability is always an extremely important object for pharmaceutical compositions.

The term "absorption" used herein means the absorption of Compound A into the body of a subject to whom Compound A has been administered. The absorption can be confirmed using area under blood concentration-time curve (AUC), maximum blood concentration (Cmax), etc. after the dissolved Compound A has been absorbed into the body of a subject, as described above. The improvement of absorption can be judged based on an increase in the AUC or Cmax value. Moreover, the absorption rate of Compound A after administration of a pharmaceutical formulation can be evaluated based on time to attain maximum blood concentration (Tmax). As a result of the improvement of absorption evaluated by these parameters, the intended effects of Compound A can be more favorably exhibited, thereby leading to optimization of the administration schedule.

Furthermore, the term "manufacturability" used herein means a property capable of easily producing a pharmaceutical composition comprising an active ingredient and sodium alkyl sulfate, and it includes a property capable of easily manufacturing a pharmaceutical composition having excellent lubricative property or flowability. In the present invention, it has been revealed that the ingredient satisfying all of the dissolution, absorption, and manufacturability is sodium alkyl sulfate described above.

The term "lubricative property" used herein means the property that powders, such as granulated products or granules used in the production of a tablet, do not adhere to a tableting machine or the like. The lubricative property can be confirmed by not observing "sticking", by which a pharmaceutical formulation adheres to the punch of a tableting machine, or by not observing "binding" by which a pharmaceutical formulation adheres to the die thereof. The lubricative property can also be confirmed by the fact that the ejection force generated upon the ejection of a tablet does not increase. By improving the lubricative property upon the production of a pharmaceutical formulation, tablets can be produced without impairing the produced tablets or production machines such as a tableting machine.

The term "flowability" used herein means the easy flow of a pharmaceutical composition before granulation. The flowability can be evaluated based on a repose angle or compressibility index. In a fluidized bed granulation step, it is difficult to fluidize powders having significantly low flowability, and thus, it may be impossible to granulate such powders. By improving the flowability of powders, granulation of the powders can be promoted, so that homogeneous granulated products can be obtained.

The excipients used in the pharmaceutical composition of the present invention are not particularly limited to the above-described excipients, as long as they are generally used for formulations in the pharmaceutical field. For example, a glidant, an excipient, a binder, a lubricant, a coloring agent, a disintegrant and the like can be used.

Examples of glidants may include silicon dioxide, sodium silicate, talc, and magnesium stearate.

Examples of excipients may include lactose (including lactose hydrate), corn starch, microcrystalline cellulose, and D-mannitol.

Examples of binders may include hydroxypropyl cellulose, hypromellose and polyvinyl alcohol.

Examples of lubricants may include hardened oil, sucrose fatty acid ester, sodium lauryl sulfate, magnesium stearate and stearic acid.

Examples of coloring agents may include edible yellow No. 5 pigment, edible blue No. 2 pigment, edible lake pigment, iron sesquioxide, yellow iron sesquioxide, and titanium oxide.

Examples of coating agents may include hydroxypropylmethyl cellulose (hypromellose, TC-5, METOLOSE, etc.) and polyethylene glycol (PEG400, PEG1500, PEG4000, PEG6000, Macrogol 400, Macrogol 1500, Macrogol 4000, Macrogol 6000, etc.).

Examples of disintegrants may include low-substituted hydroxypropyl cellulose, corn starch, partially pregelatinized starch, microcrystalline cellulose, carmellose sodium, carmellose calcium, D-mannitol, and crospovidone. Among these, microcrystalline cellulose, D-mannitol, or crospovidone is preferable.

In the present invention, the pharmaceutical composition comprising Compound A or a pharmaceutically acceptable salt thereof and sodium alkyl sulfate may further comprise a disintegrant.

Crospovidone (cross-linked PVP) used as a disintegrant is a commercially available pharmaceutical product excipient. In the present invention, the amount of crospovidone is 1% to 20% by mass, and preferably 2% to 15% by mass, based on the amount of the entire pharmaceutical composition.

In addition, crospovidone is used in an amount of 0.1 to 20 parts by mass, preferably 0.2 to 5 parts by mass, more preferably 0.2 to 3 parts by mass, and particularly preferably 0.9 to 1.1 parts by mass, 1.4 to 1.6 parts by mass, or 1.9 to 2.1 parts by mass, relative to 1 part by mass of Compound A.

Moreover, crospovidone is used in an amount of 0.1 to 20 parts by mass, preferably 0.2 to 5 parts by mass, more preferably 0.2 to 3 parts by mass, and particularly preferably 0.9 to 1.1 parts by mass, 1.4 to 1.6 parts by mass, or 1.9 to 2.1 parts by mass, relative to 1 part by mass of sodium alkyl sulfate.

In the present invention, the pharmaceutical composition comprising Compound A or a pharmaceutically acceptable salt thereof and sodium alkyl sulfate may further comprise carmellose sodium as a disintegrant.

Carmellose sodium is a pharmaceutical product excipient. In the present invention, the amount of carmellose sodium is 1% to 10% by mass based on the amount of the entire pharmaceutical composition.

In addition, carmellose sodium is used in an amount of 0.1 to 5 parts by mass, preferably 0.2 to 2 parts by mass, and particularly preferably 0.2 to 0.4 parts by mass, or 0.9 to 1.2 parts by mass, relative to 1 part by mass of Compound A.

Moreover, carmellose sodium is used in an amount of 0.1 to 5 parts by mass, more preferably 0.2 to 2 parts by mass, and particularly preferably 0.2 to 0.4 parts by mass, or 0.9 to 1.2 parts by mass, relative to 1 part by mass of sodium alkyl sulfate.

In the present invention, the pharmaceutical composition comprising Compound A or a pharmaceutically acceptable salt thereof and sodium alkyl sulfate may further comprise carmellose calcium as a disintegrant. In the present invention, the amount of carmellose calcium is 1% to 10% by mass based on the amount of the entire pharmaceutical composition.

In addition, carmellose calcium is used in an amount of 0.1 to 5 parts by mass, preferably 0.2 to 2 parts by mass, and particularly preferably 0.2 to 0.4 parts by mass, or 0.9 to 1.2 parts by mass, relative to 1 part by mass of Compound A.

Moreover, carmellose calcium is used in an amount of 0.1 to 5 parts by mass, more preferably 0.2 to 2 parts by mass, and particularly preferably 0.2 to 0.4 parts by mass, or 0.9 to 1.2 parts by mass, relative to 1 part by mass of sodium alkyl sulfate.

In the present invention, the pharmaceutical composition comprising Compound A or a pharmaceutically acceptable salt thereof and sodium alkyl sulfate may further comprise D-mannitol as a disintegrant.

D-mannitol used as a disintegrant has been known as a disintegrant used in an oral fast disintegrant. The amount of D-mannitol that can be used in the present invention is 10% to 80% by mass, preferably 15% to 70% by mass, and more preferably 20% to 60% by mass, based on the entire pharmaceutical composition.

Moreover, the amount of D-mannitol that can be used in the present invention is 1 to 20 parts by mass, preferably 2 to 15 parts by mass, more preferably 2 to 12 parts by mass, and particularly preferably 2 to 4 parts by mass, 6 to 8 parts by mass, or 9 to 11 parts by mass, relative to 1 part by mass of Compound A.

In the present invention, the pharmaceutical composition comprising Compound A or a pharmaceutically acceptable salt thereof and sodium alkyl sulfate may further comprise lactose as an excipient.

The amount of lactose that can be used in the present invention is 1% to 80% by mass, preferably 2% to 70% by mass, and more preferably 3% to 60% by mass, based on the entire pharmaceutical composition.

Moreover, the amount of lactose that can be used in the present invention is 1 to 30 parts by mass, preferably 1 to 10 parts by mass, more preferably 1 to 5 parts by mass, and particularly preferably 1 to 2 parts by mass, or 4 to 5 parts by mass, relative to 1 part by mass of Compound A.

The pharmaceutical composition of the present invention may be, for example, a pharmaceutical composition comprising, as an active ingredient, Compound A or a pharmaceutically acceptable salt thereof, and also comprising sodium alkyl sulfate. The pharmaceutical composition of the present invention is preferably a pharmaceutical composition comprising, as an active ingredient, Compound A or a pharmaceutically acceptable salt thereof, and also comprising sodium lauryl sulfate.

The pharmaceutical composition of the present invention is more preferably a pharmaceutical composition comprising, as an active ingredient, Compound A or a pharmaceutically acceptable salt thereof, and comprising 0.05 to 15 parts by mass of sodium lauryl sulfate relative to 1 part by mass of Compound A.

The pharmaceutical composition of the present invention is even more preferably a pharmaceutical composition comprising, as an active ingredient, Compound A or a pharmaceutically acceptable salt thereof, and comprising 0.1 to 10 parts by mass of sodium lauryl sulfate relative to 1 part by mass of Compound A.

The pharmaceutical composition of the present invention is further preferably a pharmaceutical composition comprising, as an active ingredient, Compound A or a pharmaceutically acceptable salt thereof, and comprising 0.2 to 5 parts by mass of sodium lauryl sulfate relative to 1 part by mass of Compound A.

The pharmaceutical composition of the present invention is further preferably a pharmaceutical composition comprising, as an active ingredient, Compound A or a pharmaceutically acceptable salt thereof, and comprising 0.25 to 3 parts by mass of sodium lauryl sulfate relative to 1 part by mass of Compound A.

The pharmaceutical composition of the present invention is still further preferably a pharmaceutical composition comprising, as an active ingredient, Compound A or a pharmaceutically acceptable salt thereof, and also comprising 0.75 to 1.5 parts by mass of sodium lauryl sulfate relative to 1 part by mass of Compound A.

The pharmaceutical composition of the present invention is still further preferably a pharmaceutical composition comprising, as an active ingredient, Compound A or a pharmaceutically acceptable salt thereof, and also comprising 1 part by mass of sodium lauryl sulfate relative to 1 part by mass of Compound A.

The pharmaceutical composition of the present invention is particularly preferably a pharmaceutical composition comprising, as an active ingredient, Compound A or a pharmaceutically acceptable salt thereof, also comprising 1 part by mass of sodium lauryl sulfate relative to 1 part by mass of Compound A, and further comprising one excipient selected from the group consisting of crospovidone, carmellose sodium, and carmellose calcium.

In another embodiment, the pharmaceutical composition of the present invention is preferably a pharmaceutical composition comprising, as an active ingredient, Compound A or a pharmaceutically acceptable salt thereof, also comprising sodium lauryl sulfate, and further comprising one or more excipients selected from the group consisting of crospovidone, carmellose sodium, and carmellose calcium.

The pharmaceutical composition of the present invention is more preferably a pharmaceutical composition comprising, as an active ingredient, Compound A or a pharmaceutically acceptable salt thereof, also comprising sodium lauryl sulfate, and further comprising 0.1 to 20 parts by mass of one excipient selected from the group consisting of crospovidone, carmellose sodium, and carmellose calcium, relative to 1 part by mass of Compound A.

The pharmaceutical composition of the present invention is even more preferably a pharmaceutical composition comprising, as an active ingredient, Compound A or a pharmaceutically acceptable salt thereof, also comprising sodium lauryl sulfate, and further comprising 0.2 to 5 parts by mass of crospovidone relative to 1 part by mass of Compound A.

The pharmaceutical composition of the present invention is further preferably a pharmaceutical composition comprising, as an active ingredient, Compound A or a pharmaceutically acceptable salt thereof, also comprising sodium lauryl sulfate, and further comprising 0.2 to 3 parts by mass of crospovidone relative to 1 part by mass of Compound A.

The pharmaceutical composition of the present invention is particularly preferably a pharmaceutical composition comprising, as an active ingredient, Compound A or a pharmaceutically acceptable salt thereof, also comprising sodium lauryl sulfate, and further comprising 0.9 to 1.1 parts by mass, 1.4 to 1.6 parts by mass, or 1.9 to 2.1 parts by mass of crospovidone, relative to 1 part by mass of Compound A.

In another embodiment, the pharmaceutical composition of the present invention is preferably a pharmaceutical composition comprising, as an active ingredient, Compound A or a pharmaceutically acceptable salt thereof, also comprising sodium lauryl sulfate, and further comprising crospovidone.

The pharmaceutical composition of the present invention is more preferably a pharmaceutical composition comprising, as an active ingredient, Compound A or a pharmaceutically acceptable salt thereof, also comprising 0.1 to 10 parts by mass of sodium lauryl sulfate relative to 1 part by mass of Compound A, and further comprising 0.1 to 20 parts by mass of crospovidone relative to 1 part by mass of Compound A.

The pharmaceutical composition of the present invention is even more preferably a pharmaceutical composition comprising, as an active ingredient, Compound A or a pharmaceutically acceptable salt thereof, also comprising 0.25 to 3 parts by mass of sodium lauryl sulfate relative to 1 part by mass of Compound A, and further comprising 0.2 to 5 parts by mass of crospovidone relative to 1 part by mass of Compound A.

The pharmaceutical composition of the present invention is further preferably a pharmaceutical composition comprising, as an active ingredient, Compound A or a pharmaceutically acceptable salt thereof, also comprising 0.75 to 1.5 parts by mass of sodium lauryl sulfate relative to 1 part by mass of Compound A, and further comprising 0.2 to 3 parts by mass of crospovidone relative to 1 part by mass of Compound A.

The pharmaceutical composition of the present invention is particularly preferably a pharmaceutical composition comprising, as an active ingredient, Compound A or a pharmaceutically acceptable salt thereof, also comprising 1 part by mass of sodium lauryl sulfate relative to 1 part by mass of Compound A, and further comprising 0.9 to 1.1 parts by mass, 1.4 to 1.6 parts by mass, or 1.9 to 2.1 parts by mass of crospovidone, relative to 1 part by mass of Compound A.

In another embodiment, the pharmaceutical composition of the present invention is preferably a pharmaceutical composition comprising, as an active ingredient, Compound A or a pharmaceutically acceptable salt thereof, also comprising sodium lauryl sulfate, and further comprising one or more excipients selected from the group consisting of crospovidone, carmellose sodium, and carmellose calcium.

The pharmaceutical composition of the present invention is more preferably a pharmaceutical composition comprising, as an active ingredient, Compound A or a pharmaceutically acceptable salt thereof, also comprising sodium lauryl sulfate, further comprising one or more excipients selected from the group consisting of crospovidone, carmellose sodium, and carmellose calcium, and further comprising D-mannitol.

The pharmaceutical composition of the present invention is even more preferably a pharmaceutical composition comprising, as an active ingredient, Compound A or a pharmaceutically acceptable salt thereof, also comprising sodium lauryl sulfate, further comprising one or more excipients selected from the group consisting of crospovidone, carmellose sodium, and carmellose calcium, and further comprising 1 to 20 parts by mass of D-mannitol relative to 1 part by mass of Compound A.

The pharmaceutical composition of the present invention is further preferably a pharmaceutical composition comprising, as an active ingredient, Compound A or a pharmaceutically acceptable salt thereof, also comprising sodium lauryl sulfate, further comprising one or more excipients selected from the group consisting of crospovidone, carmellose sodium, and carmellose calcium, and further comprising 2 to 12 parts by mass of D-mannitol relative to 1 part by mass of Compound A.

The pharmaceutical composition of the present invention is particularly preferably a pharmaceutical composition comprising, as an active ingredient, Compound A or a pharmaceutically acceptable salt thereof, also comprising sodium lauryl sulfate, further comprising one or more excipients selected from the group consisting of crospovidone, carmellose sodium, and carmellose calcium, and further comprising 2 to 4 parts by mass, 6 to 8 parts by mass, or 9 to 11 parts by mass of D-mannitol, relative to 1 part by mass of Compound A.

In a further embodiment, the pharmaceutical composition of the present invention is preferably a pharmaceutical composition comprising, as an active ingredient, Compound A or a pharmaceutically acceptable salt thereof, also comprising sodium lauryl sulfate, further comprising one or more excipients selected from the group consisting of crospovidone, carmellose sodium, and carmellose calcium, and further comprising one or more excipients selected from the group consisting of D-mannitol and lactose.

The pharmaceutical composition of the present invention is more preferably a pharmaceutical composition comprising, as an active ingredient, Compound A or a pharmaceutically acceptable salt thereof, also comprising sodium lauryl sulfate, further comprising one or more excipients selected from the group consisting of crospovidone, carmellose sodium, and carmellose calcium, further comprising D-mannitol, and further comprising 1 to 30 parts by mass of lactose relative to 1 part by mass of Compound A.

The pharmaceutical composition of the present invention is further preferably a pharmaceutical composition comprising, as an active ingredient, Compound A or a pharmaceutically acceptable salt thereof, also comprising sodium lauryl sulfate, further comprising one or more excipients selected from the group consisting of crospovidone, carmellose sodium, and carmellose calcium, further comprising D-mannitol, and further comprising 1 to 10 parts by mass of lactose relative to 1 part by mass of Compound A.

The pharmaceutical composition of the present invention is particularly preferably a pharmaceutical composition comprising, as an active ingredient, Compound A or a pharmaceutically acceptable salt thereof, also comprising sodium lauryl sulfate, further comprising one or more excipients selected from the group consisting of crospovidone, carmellose sodium, and carmellose calcium, further comprising 2 to 12 parts by mass of D-mannitol relative to 1 part by mass of Compound A, and further comprising 1 to 5 parts by mass of lactose relative to 1 part by mass of Compound A.

In a further embodiment, the pharmaceutical composition of the present invention is preferably a pharmaceutical composition comprising, as an active ingredient, Compound A or a pharmaceutically acceptable salt thereof, also comprising sodium lauryl sulfate, and further comprising D-mannitol.

The pharmaceutical composition of the present invention is more preferably a pharmaceutical composition comprising, as an active ingredient, Compound A or a pharmaceutically acceptable salt thereof, also comprising sodium lauryl sulfate, and further comprising 1 to 20 parts by mass of D-mannitol relative to 1 part by mass of Compound A.

The pharmaceutical composition of the present invention is further preferably a pharmaceutical composition comprising, as an active ingredient, Compound A or a pharmaceutically acceptable salt thereof, also comprising sodium lauryl sulfate, and further comprising 2 to 15 parts by mass of D-mannitol relative to 1 part by mass of Compound A.

The pharmaceutical composition of the present invention is particularly preferably a pharmaceutical composition comprising, as an active ingredient, Compound A or a pharmaceutically acceptable salt thereof, also comprising sodium lauryl sulfate, further comprising 2 to 12 parts by mass of D-mannitol relative to 1 part by mass of Compound A, and further comprising one or more excipients selected from the group consisting of crospovidone, carmellose sodium, and carmellose calcium.

In a further embodiment, the pharmaceutical composition of the present invention is preferably a pharmaceutical composition comprising, as an active ingredient, Compound A or a pharmaceutically acceptable salt thereof, also comprising sodium lauryl sulfate, and further comprising lactose.

The pharmaceutical composition of the present invention is more preferably a pharmaceutical composition comprising, as an active ingredient, Compound A or a pharmaceutically acceptable salt thereof, also comprising sodium lauryl sulfate, and further comprising 1 to 30 parts by mass of lactose relative to 1 part by mass of Compound A. The pharmaceutical composition of the present invention is further preferably a pharmaceutical composition comprising, as an active ingredient, Compound A or a pharmaceutically acceptable salt thereof, also comprising sodium lauryl sulfate, and further comprising 1 to 10 parts by mass of lactose relative to 1 part by mass of Compound A.

The pharmaceutical composition of the present invention is particularly preferably a pharmaceutical composition comprising, as an active ingredient, Compound A or a pharmaceutically acceptable salt thereof, also comprising sodium lauryl sulfate, further comprising 1 to 5 parts by mass of lactose relative to 1 part by mass of Compound A, and further comprising one or more excipients selected from the group consisting of crospovidone, carmellose sodium, and carmellose calcium.

In a further embodiment, the pharmaceutical composition of the present invention is preferably a pharmaceutical composition comprising, as an active ingredient, Compound A or a pharmaceutically acceptable salt thereof, and also comprising sodium lauryl sulfate, crospovidone, lactose, and D-mannitol.

The pharmaceutical composition of the present invention is more preferably a pharmaceutical composition comprising, as an active ingredient, Compound A or a pharmaceutically acceptable salt thereof, and also comprising 0.01 to 25 parts by mass of sodium lauryl sulfate, 0.1 to 20 parts by mass of crospovidone, 0.1 to 20 parts by mass of D-mannitol, and 0.1 to 30 parts by mass of lactose, relative to 1 part by mass of Compound A.

The pharmaceutical composition of the present invention is even more preferably a pharmaceutical composition comprising, as an active ingredient, Compound A or a pharmaceutically acceptable salt thereof, and also comprising 0.1 to 10 parts by mass of sodium lauryl sulfate, 0.1 to 20 parts by mass of crospovidone, 0.1 to 20 parts by mass of D-mannitol, and 0.1 to 30 parts by mass of lactose, relative to 1 part by mass of Compound A.

The pharmaceutical composition of the present invention is further preferably a pharmaceutical composition comprising, as an active ingredient, Compound A or a pharmaceutically acceptable salt thereof, and also comprising 0.2 to 5 parts by mass of sodium lauryl sulfate, 0.1 to 20 parts by mass of crospovidone, 0.1 to 20 parts by mass of D-mannitol, and 0.1 to 30 parts by mass of lactose, relative to 1 part by mass of Compound A.

The pharmaceutical composition of the present invention is still further preferably a pharmaceutical composition comprising, as an active ingredient, Compound A or a pharmaceutically acceptable salt thereof, and also comprising 0.25 to 3 parts by mass of sodium lauryl sulfate, 0.1 to 20 parts by mass of crospovidone, 0.1 to 20 parts by mass of D-mannitol, and 0.1 to 30 parts by mass of lactose, relative to 1 part by mass of Compound A.

The pharmaceutical composition of the present invention is still further preferably a pharmaceutical composition comprising, as an active ingredient, Compound A or a pharmaceutically acceptable salt thereof, and also comprising 0.75 to 1.5 parts by mass of sodium lauryl sulfate, 0.1 to 20 parts by mass of crospovidone, 0.1 to 20 parts by mass of D-mannitol, and 0.1 to 30 parts by mass of lactose, relative to 1 part by mass of Compound A.

The pharmaceutical composition of the present invention is still further preferably a pharmaceutical composition comprising, as an active ingredient, Compound A or a pharmaceutically acceptable salt thereof, and also comprising 0.75 to 1.5 parts by mass of sodium lauryl sulfate, 0.2 to 5 parts by mass of crospovidone, 0.1 to 20 parts by mass of D-mannitol, and 0.1 to 30 parts by mass of lactose, relative to 1 part by mass of Compound A.

The pharmaceutical composition of the present invention is still further preferably a pharmaceutical composition comprising, as an active ingredient, Compound A or a pharmaceutically acceptable salt thereof, and also comprising 0.75 to 1.5 parts by mass of sodium lauryl sulfate, 0.2 to 3 parts by mass of crospovidone, 0.1 to 20 parts by mass of D-mannitol, and 0.1 to 30 parts by mass of lactose, relative to 1 part by mass of Compound A.

The pharmaceutical composition of the present invention is still further preferably a pharmaceutical composition comprising, as an active ingredient, Compound A or a pharmaceutically acceptable salt thereof, and also comprising 0.75 to 1.5 parts by mass of sodium lauryl sulfate, 0.2 to 3 parts by mass of crospovidone, 2 to 15 parts by mass of D-mannitol, and 1 to 10 parts by mass of lactose, relative to 1 part by mass of Compound A.

The pharmaceutical composition of the present invention is much further preferably a pharmaceutical composition comprising, as an active ingredient, Compound A or a pharmaceutically acceptable salt thereof, and also comprising 0.75 to 1.5 parts by mass of sodium lauryl sulfate, 0.2 to 3 parts by mass of crospovidone, 2 to 12 parts by mass of D-mannitol, and 1 to 5 parts by mass of lactose, relative to 1 part by mass of Compound A.

The pharmaceutical composition of the present invention is particularly preferably a pharmaceutical composition comprising, as an active ingredient, Compound A or a pharmaceutically acceptable salt thereof, and also comprising 1 part by mass of sodium lauryl sulfate, 0.9 to 1.1 parts by mass, 1.4 to 1.6 parts by mass, or 1.9 to 2.1 parts by mass of crospovidone, 2 to 4 parts by mass, 6 to 8 parts by mass, or 9 to 11 parts by mass of D-mannitol, and 1 to 2 parts by mass, or 4 to 5 parts by mass of lactose, relative to 1 part by mass of Compound A.

For the pharmaceutical composition of the present invention, a common administration route, such as oral administration, transdermal administration, intraperitoneal administration or intravenous administration, can be adopted. Among these, oral administration is preferable. Accordingly, in a preferred embodiment, the pharmaceutical composition of the present invention is a pharmaceutical composition for oral administration comprising Compound A and sodium alkyl sulfate.

Examples of pharmaceutical compositions for oral administration may include, but are not limited to, syrup, a powder, a granule, a tablet, and a capsule.

The pharmaceutical composition of the present invention can be produced by a known method for producing a pharmaceutical formulation. For example, a granulated material can be produced by a granulation method, a fluidized bed granulation method, an agitation granulation method, a tumbling fluidized bed granulation method, an extrusion granulation method, a spray granulation method, a crushing granulation method, and the like.

When the pharmaceutical composition of the present invention is formulated into a tablet, the surface of the tablet may be coated, so as to produce a pharmaceutical composition for oral administration, which is stable and easy to take. Coating includes film coating and sugar coating. Examples of a coating agent may include hypromellose, ethyl cellulose, hydroxypropyl cellulose, polyvinyl alcohol, and white sugar.

In addition, in order to obtain a pharmaceutical composition for oral administration that is easy to take, various types of flavors, such as orange and lemon flavors, can be used as flavoring agents, and also, 1-menthol, camphor, mint, and the like can be used as corrigents for the pharmaceutical composition of the present invention.

Since Compound A has excellent EGFR inhibitory activity, the pharmaceutical composition of the present invention is useful as an antitumor agent. The cancer as a target is not particularly limited, and examples of the cancer may include head and neck cancer, gastrointestinal cancer [e.g., esophageal cancer, stomach cancer, gastrointestinal stromal tumor, duodenal cancer, liver cancer, biliary tract cancer (for example, gallbladder and/or bile duct cancer, etc.), pancreatic cancer, small intestine cancer, large bowel cancer (for example, colorectal cancer, colon cancer, rectal cancer, etc.), etc.], lung cancer, breast cancer, ovarian cancer, uterine cancer (for example, cervical cancer, endometrial cancer, etc.), kidney cancer, bladder cancer, prostate cancer, urothelial carcinoma, bone and soft tissue sarcoma, blood cancer (for example, B-cell lymphoma, chronic lymphocytic leukemia, peripheral T-cell lymphoma, myelodysplastic syndrome, acute myelogenous leukemia, acute lymphocytic leukemia, etc.), multiple myeloma, skin cancer, and mesothelioma.

Accordingly, the present invention provides a pharmaceutical composition for use in treating or preventing tumor selected from head and neck cancer, gastrointestinal cancer [e.g., esophageal cancer, stomach cancer, gastrointestinal stromal tumor, duodenal cancer, liver cancer, biliary tract cancer (for example, gallbladder and/or bile duct cancer, etc.), pancreatic cancer, small intestine cancer, large bowel cancer (for example, colorectal cancer, colon cancer, rectal cancer, etc.), etc.], lung cancer, breast cancer, ovarian cancer, uterine cancer (for example, cervical cancer, endometrial cancer, etc.), kidney cancer, bladder cancer, prostate cancer, urothelial carcinoma, bone and soft tissue sarcoma, blood cancer (for example, B-cell lymphoma, chronic lymphocytic leukemia, peripheral T-cell lymphoma, myelodysplastic syndrome, acute myelogenous leukemia, acute lymphocytic leukemia, etc.), multiple myeloma, skin cancer, and mesothelioma.

In another aspect, the present invention provides a method for improving the dissolution of Compound A from a pharmaceutical composition comprising Compound A or a pharmaceutically acceptable salt thereof, which is characterized in that it comprises adding sodium lauryl sulfate to the pharmaceutical composition.

In another aspect, the present invention provides a method for improving the absorption of Compound A, which is characterized in that it comprises adding sodium lauryl sulfate to a pharmaceutical composition comprising Compound A or a pharmaceutically acceptable salt thereof.

In another aspect, the present invention provides a method for improving manufacturability, which is characterized in that it comprises adding sodium lauryl sulfate to a pharmaceutical composition comprising Compound A or a pharmaceutically acceptable salt thereof.

In another aspect, the present invention provides use of sodium lauryl sulfate for improving the dissolution of Compound A or a pharmaceutically acceptable salt thereof.

In another aspect, the present invention provides use of sodium lauryl sulfate for improving the absorption of Compound A or a pharmaceutically acceptable salt thereof.

In another aspect, the present invention provides use of sodium lauryl sulfate for improving the manufacturability of a pharmaceutical composition comprising Compound A or a pharmaceutically acceptable salt thereof.

In another aspect, the present invention provides use of sodium lauryl sulfate for producing a pharmaceutical composition comprising Compound A or a pharmaceutically acceptable salt thereof.

EXAMPLES

Hereinafter, the present invention will be more specifically described by way of examples. However, these examples are not intended to limit the scope of the present invention. The present invention is sufficiently described in the examples, but it will be understood that various alternations or modifications can be carried out by a person skilled in the art. Accordingly, such alterations or modifications are included in the present invention, unless they are deviated from the scope of the present invention.

Various types of reagents used in the examples were commercially available products, unless otherwise specified.

[Test Example 1] Solubility Test

As described in Formulation Examples 1 and 2 and Comparative Examples 1 to 15, test solutions, in which (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one (Compound A) was combined with various types of surfactants, were prepared as follows, and the obtained test solutions were used in solubility tests, as described below.

Formulation Example 1

0.05 g of Sodium lauryl sulfate (manufactured by SERVA, Research grade) was dissolved in 50 mM phosphate buffer (50 mL) of pH 6.8, and 25 mg of Compound A was then suspended in the solution, followed by heating the suspension at 37° C. for 60 minutes, to obtain a test sample.

Formulation Example 2

0.5 g of Sodium lauryl sulfate was dissolved in 50 mM phosphate buffer (50 mL) of pH 6.8, and 25 mg of Compound A was then suspended in the solution, followed by heating the suspension at 37° C. for 60 minutes, to obtain a test sample.

Comparative Example 1

25 mg of Compound A was suspended in Solution 2 (50 mL) of pH 6.8 for the dissolution test of the Japanese Pharmacopeia, and the obtained suspension was heated at 37° C. for 60 minutes to obtain a test sample.

Comparative Example 2

0.05 g of Sucrose fatty acid monoester (DK Ester SS, manufactured by DKS Co. Ltd.) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 3

0.5 g of Sucrose fatty acid monoester (DK Ester SS) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 4

0.05 g of PEG6000 (Macrogol 6000, manufactured by NOF CORPORATION) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 5

0.5 g of PEG6000 was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 6

0.05 g of Poloxamer (Lutrol F68, manufactured by BASF Corporation) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 7

0.5 g of Poloxamer (Lutrol F68) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 8

0.05 g of Polyoxyethylene sorbitan monolaurate (Tween 20, manufactured by Tokyo Chemical Industry Co., Ltd.) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 9

0.5 g of Polyoxyethylene sorbitan monolaurate (Tween 20) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 10

0.05 g of Polyoxyethylene sorbitan monostearate (Tween 60, manufactured by Tokyo Chemical Industry Co., Ltd.) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 11

0.5 g of Polyoxyethylene sorbitan monostearate (Tween 60) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 12

0.05 g of Polyoxyethylene sorbitan monooleate (Tween 80, manufactured by Tokyo Chemical Industry Co., Ltd.) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 13

0.5 g of Polyoxyethylene sorbitan monooleate (Tween 80) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 14

0.05 g of Polyoxyethylene castor oil (Cremophor EL, manufactured by Sigma-Aldrich) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

Comparative Example 15

0.5 g of Polyoxyethylene castor oil (Cremophor EL) was dissolved in Solution 2 (50 mL) of pH 6.8 for the dissolution test of the Japanese Pharmacopeia, and 25 mg of Compound A was then suspended in the solution, followed by heating the suspension at 37° C. for 60 minutes, to obtain a test sample.

The above-described Formulation Examples 1 and 2 and Comparative Examples 1 to 15 were measured in terms of solubility using high performance liquid chromatography.

Apparatus: LC-2010C (Shimadzu Corporation)

Measurement wavelength: 300 nm

The handling of apparatuses, including data processing, was carried out according to the method and procedures instructed for each apparatus. The compositions of Formulation Examples 1 and 2 and Comparative Examples 1 to 15 and the results of the present test are shown in Tables 1 and 2.

TABLE 1

| (Unit: part by mass) | Formulation Example 1 | Formulation Example 2 | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|
| Compound A | 25 | 25 | 25 | 25 | 25 | 25 | 25 | 25 | 25 |
| Sodium lauryl sulfate | 50 | 500 | — | — | — | — | — | — | — |
| Sucrose fatty acid monoester | — | — | — | 50 | 500 | — | — | — | — |
| Polyethylene glycol | — | — | — | — | — | 50 | 500 | — | — |
| Poloxamer | — | — | — | — | — | — | — | 50 | 500 |
| Polyoxyethylene sorbitan monolaurate | — | — | — | — | — | — | — | — | — |
| Polyoxyethylene sorbitan monostearate | — | — | — | — | — | — | — | — | — |
| Polyoxyethylene sorbitan monooleate | — | — | — | — | — | — | — | — | — |
| Polyoxyethylene castor oil | — | — | — | — | — | — | — | — | — |
| Dissolution in Solution 2 (μg/mL), Japanese Pharmacopeia, Dissolution Test | 64 | 1439 | 3 | 33.9 | 250.3 | 3.5 | 4.8 | 3.7 | 6.6 |

TABLE 2

| (Unit: part by mass) | Comparative Example 8 | Comparative Example 9 | Comparative Example 10 | Comparative Example 11 | Comparative Example 12 | Comparative Example 13 | Comparative Example 14 | Comparative Example 15 |
|---|---|---|---|---|---|---|---|---|
| Compound A | 25 | 25 | 25 | 25 | 25 | 25 | 25 | 25 |
| Sodium lauryl sulfate | — | — | — | — | — | — | — | — |
| Sucrose fatty acid monoester | — | — | — | — | — | — | — | — |
| Polyethylene glycol | — | — | — | — | — | — | — | — |
| Poloxamer | — | — | — | — | — | — | — | — |
| Polyoxyethylene sorbitan monolaurate | 50 | 500 | — | — | — | — | — | — |
| Polyoxyethylene sorbitan monostearate | — | — | 50 | 500 | — | — | — | — |
| Polyoxyethylene sorbitan monooleate | — | — | — | — | 50 | 500 | — | — |
| Polyoxyethylene castor oil | — | — | — | — | — | — | 50 | 500 |
| Dissolution in Solution 2 (μg/mL), Japanese Pharmacopeia, Dissolution Test | 8.7 | 57.4 | 10.7 | 61.6 | 10.3 | 62.9 | 9.8 | 62.7 |

As shown in Tables 1 and 2, when compared with Comparative Example 1, in which no surfactants were used, although the solubility of Compound A hardly changed by addition of some surfactants, the effect of improving solubility was found by addition of several surfactants including sodium lauryl sulfate. Among others, sodium lauryl sulfate and sucrose fatty acid monoester provided a high effect of improving solubility. In particular, sodium lauryl sulfate exhibited high solubility in a 0.1% solution (Formulation Example 1), and it was found that the solubility of Compound A in 1.0% solution (Formulation Example 2) becomes approximately 500 times higher than that in the case of not adding a surfactant (Comparative Example 1).

[Test Example 2] Absorption Test

Using sodium lauryl sulfate and sucrose fatty acid monoester, which provided a favorable effect of improving the solubility of Compound A in Test Example 1, an absorption test was carried out as follows.

Formulation Example 3

2.4 g of Sodium lauryl sulfate (Wako Corporation, for biochemical use) was dissolved in water (40 mL), and 0.8 g of Compound A was then suspended in the solution to obtain a suspension of Compound A.

Comparative Example 16

0.8 g of Compound A was suspended in 0.5% hypromellose aqueous solution (40 mL), commonly used in absorption tests for pharmaceutical products, to obtain a suspension of Compound A.

Comparative Example 17

2.4 g of Sucrose fatty acid monoester (DK Ester SS) was dissolved in water (40 mL), and 0.8 g of Compound A was then suspended in the solution to obtain a suspension of Compound A.

Formulation Example 3 and Comparative Examples 16 and 17 were subjected to the following absorption test.
<Absorption Experiment Conditions>
Animals: Beagle dogs (KITAYAMA LABES CO., LTD., 3 male dogs)
Meal conditions: Fasting for 20 hours from previous day
Dose: 100 mg/body
Administration sample: 0.82 g each of Formulation Example 3 and Comparative Examples 16 and 17
Administration method: Oral administration with 50 mL of water, using a sonde Pre-treatment: Thirty minutes before administration of the administration sample, atropine sulfate solution for intravenous injection (10 μg/0.1 mL/kg) and pentagastrin solution for intramuscular injection (10 μg/0.1 mL/kg) were intravenously or intramuscularly administered to the dogs respectively, and thereafter, the pentagastrin solution for intramuscular injection (10 g/0.1 mL/kg) was intramuscularly administered thereto, twice, with an interval of 45 minutes. Thirty minutes, 1 hour, 1.5 hours, 2 hours, 4 hours, and 8 hours after the oral administration of the formulation example and the comparative examples, blood samples were collected from each animal, and the blood concentration of Compound A were measured (according to liquid chromatography/mass spectrometry), and the AUC and Cmax values were calculated. The results are shown in Table 3.

TABLE 3

| (Unit: part by mass) | Formulation Example | Comparative Example | |
|---|---|---|---|
| | 3 | 16 | 17 |
| Compound A | 1 | 1 | 1 |
| Sodium lauryl sulfate | 3 | — | — |
| Sucrose fatty acid monoester | — | — | 3 |
| AUC ng · hr/mL | 6412 ± 2470 | 2126 ± 1264 | 3197 ± 1441 |
| Cmax ng/mL | 1877 ± 716 | 764 ± 411 | 740 ± 451 |

As shown in Table 3, Comparative Example 17 comprising sucrose fatty acid monoester together with Compound A exhibited comparative absorption as Comparative Example 16 that was a suspension of Compound A only. On the other hand, Formulation Example 3 comprising sodium lauryl sulfate together with Compound A exhibited the absorption of Compound A that was much higher than Comparative Example 17 comprising the equal amount of sucrose fatty acid monoester. Accordingly, it became clear that sodium lauryl sulfate is useful for the improvement of absorption of Compound A.

[Test Example 3] Absorption Test

Granules comprising Compound A and sodium lauryl sulfate were prepared as follows, and an absorption test was carried out in the same manner as Test Example 2.

Formulation Example 4

2 g of Compound A, 0.5 g of sodium lauryl sulfate, 9.5 g of lactose, and 4 g of corn starch were mixed with one another in a glass bottle for 1 minute. The total amount of the obtained mixture was sieved through a sieve with an opening of 500 m, and then was blended again in a glass bottle for 1 minute. While blending the mixture using a pestle and a mortar, 3400 μL of 10% low viscosity hydroxypropyl cellulose (HPC-SL) was added thereto. The total amount of the obtained mixture was sieved through a sieve with an opening of 850 μm, and the resultant was dried using a moisture meter (AND, MX-50) at 70° C. Thereafter, the total amount of the resultant was further sieved through a sieve with an opening of 1000 m, so as to obtain granules of Compound A.

Formulation Example 5

2 g of Compound A, 2 g of sodium lauryl sulfate, 8.4 g of lactose, and 3.6 g of corn starch were mixed with one another in a glass bottle for 1 minute. The total amount of the obtained mixture was sieved through a sieve with an opening of 500 μm, and then was blended in a glass bottle for 1 minute. While blending the mixture using a pestle and a mortar, 3200 μL of 10% low viscosity hydroxypropyl cellulose (HPC-SL) was added thereto. The total amount of the obtained mixture was sieved through a sieve with an opening of 850 μm, and the resultant was dried using a moisture meter (AND, MX-50) at 70° C. Thereafter, the total amount of the resultant was further sieved through a sieve with an opening of 1000 μm, so as to obtain granules of Compound A.

Formulation Example 6

1.4 g of Compound A, 4.2 g of sodium lauryl sulfate, 3.9 g of lactose, and 1.9 g of corn starch were mixed with one another in a glass bottle for 1 minute. The total amount of the obtained mixture was sieved through a sieve with an opening of 500 μm, and then was blended in a glass bottle for 1 minute. While 6.4 g of the obtained mixture was blended using a pestle and a mortar, 1330 μL of 10% low viscosity hydroxypropyl cellulose (HPC-SL) was added thereto. The total amount of the obtained mixture was sieved through a sieve with an opening of 850 μm, and the resultant was dried using a moisture meter (AND, MX-50) at 70° C. Thereafter, the total amount of the resultant was further sieved through a sieve with an opening of 1000 μm, so as to obtain granules of Compound A.

Formulation Examples 4 to 6, and Comparative Examples 16 used in Test Example 2 were subjected to the following absorption test.

<Absorption Experiment Conditions>
Animals: Beagle dogs (KITAYAMA LABES CO., LTD., 3 male dogs)
Meal conditions: Fasting for 20 hours from previous day
Dose: 100 mg/body
Administration sample: 0.82 g each of Formulation Examples 4 to 6 and Comparative Example 16
Administration method: Oral administration with 50 mL of water
Pre-treatment: Thirty minutes before administration of the administration sample, atropine sulfate solution for intravenous injection (10 μg/0.1 mL/kg) and pentagastrin solution for intramuscular injection (10 μg/0.1 mL/kg) were intravenously or intramuscularly administered to the dogs respectively, and thereafter, the pentagastrin solution for intramuscular injection (10 g/0.1 mL/kg) was intramuscularly administered thereto, twice, with an interval of 45 minutes.

In the same manner as Test Example 2, 30 minutes, 1 hour, 1.5 hours, 2 hours, 4 hours, and 8 hours after the oral administration of the formulation examples and the comparative example, blood samples were collected from each animal, and the blood concentration of Compound A were measured (according to liquid chromatography/mass spectrometry), and the AUC and Cmax values were then calculated. The results are shown in Table 4.

TABLE 4

| | Formulation Example | | | Comparative Example |
|---|---|---|---|---|
| (Unit: part by mass) | 4 | 5 | 6 | 16 |
| Compound A | 1 | 1 | 1 | 1 |
| Sodium lauryl sulfate | 0.25 | 1 | 3 | — |
| Lactose | 4.75 | 4.2 | 2.7 | |
| Corn starch | 2.0 | 1.8 | 1.3 | — |
| Low viscosity hydroxypropyl cellulose | 0.17 | 0.16 | 0.09 | — |
| AUC ng · hr/mL | 4444 ± 2666 | 6373 ± 467 | 5885 ± 2034 | 2126 ± 1264 |
| Cmax ng/mL | 936 ± 471 | 1360 ± 142 | 1700 ± 731 | 764 ± 411 |

As shown in Table 4, it was found that all types of granules comprising sodium lauryl sulfate added in an amount 0.25 times, equivalent, and 3 times of the amount of Compound A (Formulation Examples 4, 5, and 6, respectively), exhibited higher absorption than Comparative Example 16, in which only Compound A was suspended. Although Formulation Example 6 exhibited the highest Cmax value, its AUC value was the same level as that of Formulation Example 5. Hence, it was considered that higher absorption could be obtained by adding sodium lauryl sulfate in the amount equal to or greater than that of Compound A.

[Test Example 4] Evaluation of Tablet Formability and Disintegration

Studies for the purpose of improving the disintegration of a tablet comprising Compound A were conducted to select a disintegrant. Five types of candidate excipients: low-substituted hydroxypropyl cellulose (LH-21, manufactured by Shin-Etsu Chemical Co., Ltd.), crospovidone (Kollidon CL-SF, BASF Corporation), carmellose sodium (KICCOLATE, Asahi Kasei Corporation), carmellose calcium (E.C.G-505, GOTOKU CHEMICAL COMPANY LTD. ), and carboxymethyl starch sodium (Glycolith, manufactured by ROQUETTE) were each added in an amount of 3% or 10% to the total mass of a tablet comprising Compound A, and thereafter, using a universal tensile/compression testing machine (Shimadzu Corporation), tablets with the compositions shown in Table 5 below were prepared. At this time, compression pressure necessary for obtaining a target hardness (65 N), and the disintegration of the tablets were evaluated, so that disintegrants were screened. The disintegration was evaluated according to the disintegration test of the Japanese Pharmacopoeia 16th Edition, using water as a test Solution Formulation Example 7

120 g of Compound A, 120 g of sodium lauryl sulfate, 516 g of lactose, and 276 g of corn starch were mixed with one another in a polyethylene bag for 1 minute. The total amount of the obtained mixture was sieved through a sieve with an opening of 500 m, and the resultant was blended again in a polyethylene bag for 5 minutes. 340 g of the obtained mixed powders were placed in a fluidized bed granulator (Freund Corporation), and then granulated while 161 g of 7.5% low viscosity hydroxypropyl cellulose was sprayed thereon, so as to obtain a granules.

Thereafter, microcrystalline cellulose, crospovidone, and magnesium stearate were added to the obtained granulated material, followed by blending in a glass bottle. The total amount of the obtained mixture was sieved through a sieve with an opening of 850 m, and the resultant was blended again in a glass bottle to obtain mixture for compression. Using a universal tensile/compression testing machine (Shimadzu Corporation), tablets of Compound A were produced under a compression pressure suitable for obtaining a target hardness (65 N).

Formulation Example 8

Microcrystalline cellulose, crospovidone, and magnesium stearate were added to the granulated material obtained in the same manner as Formulation Example 7, followed by blending in a glass bottle. The total amount of the obtained mixture was sieved through a sieve with an opening of 850 µm, and the resultant was blended again in a glass bottle to obtain mixture for compression. Using a universal tensile/compression testing machine (Shimadzu Corporation), tablets of Compound A were produced under a compression pressure suitable for obtaining a target hardness (65 N).

Formulation Example 9

Microcrystalline cellulose, carmellose sodium, and magnesium stearate were added to the granulated material obtained in the same manner as Formulation Example 7, followed by blending in a glass bottle. The total amount of the obtained mixture was sieved through a sieve with an opening of 850 µm, and the resultant was blended again in a glass bottle to obtain mixture for compression. Using a universal tensile/compression testing machine (Shimadzu Corporation), tablets of Compound A were produced under a compression pressure suitable for obtaining a target hardness (65 N).

Formulation Example 10

Microcrystalline cellulose, carmellose sodium, and magnesium stearate were added to the granulated material obtained in the same manner as Formulation Example 7, followed by blending in a glass bottle. The total amount of the obtained mixture was sieved through a sieve with an opening of 850 µm, and the resultant was blended again in a glass bottle to obtain mixture for compression. Using a universal tensile/compression testing machine (Shimadzu Corporation), tablets of Compound A were produced under a compression pressure suitable for obtaining a target hardness (65 N).

Formulation Example 11

Microcrystalline cellulose, carmellose calcium, and magnesium stearate were added to the granulated material obtained in the same manner as Formulation Example 7, followed by blending in a glass bottle. The total amount of the obtained mixture was sieved through a sieve with an opening of 850 µm, and the resultant was blended again in a glass bottle to obtain mixture for compression. Using a universal tensile/compression testing machine (Shimadzu Corporation), tablets of Compound A were produced under a compression pressure suitable for obtaining a target hardness (65 N).

Formulation Example 12

Microcrystalline cellulose, carmellose calcium, and magnesium stearate were added to the granulated material obtained in the same manner as Formulation Example 7, followed by blending in a glass bottle. The total amount of the obtained mixture was sieved through a sieve with an opening of 850 µm, and the resultant was blended again in a glass bottle to obtain mixture for compression. Using a universal tensile/compression testing machine (Shimadzu Corporation), tablets of Compound A were produced under a compression pressure suitable for obtaining a target hardness (65 N).

Formulation Example 13

Microcrystalline cellulose, carboxymethyl starch sodium, and magnesium stearate were added to the granulated material obtained in the same manner as Formulation Example 7, followed by blending in a glass bottle. The total amount of the obtained mixture was sieved through a sieve with an opening of 850 μm, and the resultant was blended again in a glass bottle to obtain mixture for compression. Using a universal tensile/compression testing machine (Shimadzu Corporation), tablets of Compound A were produced under a compression pressure suitable for obtaining a target hardness (65 N).

Formulation Example 14

Microcrystalline cellulose, low-substituted hydroxypropyl cellulose, and magnesium stearate were added to the granulated material obtained in the same manner as Formulation Example 7, followed by blending in a glass bottle. The total amount of the obtained mixture was sieved through a sieve with an opening of 850 μm, and the resultant was blended again in a glass bottle to obtain mixture for compression. Using a universal tensile/compression testing machine (Shimadzu Corporation), tablets of Compound A were produced under a compression pressure suitable for obtaining a target hardness (65 N).

Formulation Example 15

Microcrystalline cellulose and magnesium stearate were added to the granulated material obtained in the same manner as Formulation Example 7, followed by blending in a glass bottle. The total amount of the obtained mixture was sieved through a sieve with an opening of 850 μm, and the resultant was blended again in a glass bottle to obtain mixture for compression. Using a universal tensile/compression testing machine (Shimadzu Corporation), tablets of Compound A were produced under a compression pressure suitable for obtaining a target hardness (65 N).

The results of Formulation Examples 7 to 15 regarding the disintegration test are shown in Table 5.

nellose calcium was used, tablets with a constant hardness could be prepared under a compression pressure of 10 kN or lower, and the disintegration time was within 9 minutes. In addition, crospovidone provided a reduction in the disintegration time, in comparison to Formulation Example 15 that did not comprise any candidate excipients, and the compression pressure required was low, showing the effect of improving formability. On the other hand, low-substituted hydroxypropyl cellulose and carboxymethyl starch sodium do not provide a reduction in the disintegration time, and they require a high compression pressure, showing the tendency of reducing formability. From these results, all types of disintegrants are useful for tablets, but in particular, it was suggested that crospovidone, carmellose sodium, and carmellose calcium are remarkably useful.

[Test Example 5] Tablet Formability and Disintegration Tests

Using crospovidone and carmellose sodium, which were found to provide high formability and the effect of improving the disintegration to tablets comprising Compound A and sodium lauryl sulfate in Test Example 4, and using other components, each included in the same molecular mass in all of the formulation examples, tablets were prepared as follows under the compression pressure suitable for obtaining a target hardness (60 N) with a rotary tableting machine, and then compared. The results are shown in Table 6.

Formulation Example 16

200 g of Compound A, 200 g of sodium lauryl sulfate (NIKKOL SLS, manufactured by Nikko Chemicals Co., Ltd.), 860 g of lactose, and 460 g of corn starch were mixed with one another in a polyethylene bag for 1 minute. The total amount of the obtained mixture was sieved through a sieve with an opening of 500 μm, and the resultant was then blended again in a polyethylene bag for 1 minute. The

TABLE 5

| (Unit: part by mass) | Formulation Example | | | | | | | | |
|---|---|---|---|---|---|---|---|---|---|
|  | 7 | 8 | 9 | 10 | 11 | 12 | 13 | 14 | 15 |
| Compound A | 17.8 | 19.3 | 17.8 | 19.3 | 17.8 | 19.3 | 17.8 | 17.8 | 20 |
| Sodium lauryl sulfate | 17.8 | 19.3 | 17.8 | 19.3 | 17.8 | 19.3 | 17.8 | 17.8 | 20 |
| Lactose monohydrate | 76.3 | 83.1 | 76.3 | 83.1 | 76.3 | 83.1 | 76.3 | 76.3 | 86 |
| Corn starch | 40.8 | 44.4 | 40.8 | 44.4 | 40.8 | 44.4 | 40.8 | 40.8 | 46 |
| Low viscosity hydroxypropyl cellulose | 5.3 | 5.8 | 5.3 | 5.8 | 5.3 | 5.8 | 5.3 | 5.3 | 6 |
| Crospovidone | 20 | 6 | — | — | — | — | — | — | — |
| Carmellose sodium | — | — | 20 | 6 | — | — | — | — | — |
| Carmellose calcium | — | — | — | — | 20 | 6 | — | — | — |
| Carboxymethyl starch sodium | — | — | — | — | — | — | 20 | — | — |
| Low-substituted hydroxypropyl cellulose | — | — | — | — | — | — | — | 20 | — |
| Microcrystalline cellulose CEOLUS KG-802 | 20 | 20 | 20 | 20 | 20 | 20 | 20 | 20 | 20 |
| Magnesium stearate | 2 | 2 | 2 | 2 | 2 | 2 | 2 | 2 | 2 |
| Total | 200 | 200 | 200 | 200 | 200 | 200 | 200 | 200 | 200 |
| Tableting pressure (kN) | 5.42 | 6.95 | 10.07 | 7.76 | 9.95 | 7.73 | 12.18 | 9.50 | 7.19 |
| Disintegration time (min:sec) | 5:19 | 6:53 | 6:54 | 7:14 | 7:55 | 8:03 | 8:43 | 9:38 | 9:09 |

As shown in Table 5, it was found that, with any type of disintegrant, tablets having a constant hardness could be prepared under a compression pressure of 13 kN or lower, which was in the range of pressure resistance of the punch, and that the disintegration time was within 10 minutes. In particular, when crospovidone, carmellose sodium, or carobtained mixed powders were placed in a fluidized bed granulator (Freund Corporation), and granulated while 800 g of 7.5% low viscosity hydroxypropyl cellulose was sprayed thereon, so as to obtain a granulated material. The total amount of the obtained granulated material was sieved through a sieve with an opening of 850 μm.

Thereafter, 25 g of microcrystalline cellulose, 7.5 g of crospovidone, and 2.5 g of magnesium stearate were added to 222.5 g of the sieved product of the granulated material, and were mixed with one another in a polyethylene bag. Thereafter, the obtained mixture was tableted with a tableting machine (KIKUSUI SEISAKUSHO LTD.) to obtain tablets.

Formulation Example 17

To 222.5 g of the sieved product of the granulated material obtained in the same manner as Formulation Example 16, 25 g of microcrystalline cellulose, 25 g of crospovidone, and 2.5 g of magnesium stearate were added, and were mixed with one another in a polyethylene bag. Thereafter, the obtained mixture was tableted with a tableting machine (KIKUSUI SEISAKUSHO LTD.) to obtain tablets.

Formulation Example 18

To 222.5 g of the sieved product of the granulated material obtained in the same manner as Formulation Example 16, 25 g of microcrystalline cellulose, 7.5 g of carmellose sodium, and 2.5 g of magnesium stearate were added, and were mixed with one another in a polyethylene bag. Thereafter, the obtained mixture was tableted in a tableting machine (KIKUSUI SEISAKUSHO LTD.) to obtain tablets.

Formulation Example 19

To 445 g of the sieved product of the granulated material obtained in the same manner as Formulation Example 16, 50 g of microcrystalline cellulose and 5 g of magnesium stearate were added, and were mixed with one another in a polyethylene bag. Thereafter, the obtained mixture was tableted in a tableting machine (KIKUSUI SEISAKUSHO LTD.) to obtain tablets.

TABLE 6

| (Unit: part by mass) | Formulation Example | | | |
|---|---|---|---|---|
| | 16 | 17 | 18 | 19 |
| Compound A | 20 | 20 | 20 | 20 |
| Sodium lauryl sulfate | 20 | 20 | 20 | 20 |
| Lactase monohydrate | 86 | 86 | 86 | 86 |
| Corn starch | 46 | 46 | 46 | 46 |
| Low viscosity hydroxypropyl cellulose | 6 | 6 | 6 | 6 |
| Crospovidone | 6 | 20 | — | — |
| Carmellose sodium | — | — | 6 | — |
| Microcrystalline cellulose CEOLUS KG-802 | 20 | 20 | 20 | 20 |
| Magnesium stearate | 2 | 2 | 2 | 2 |
| Total | 206 | 220 | 206 | 200 |
| Tableting pressure (kN) | 8.4-9.1 | 8.6-7.7 | 11.4-11.6 | 9.7-10.0 |
| Disintegration time (min) | 6.34 | 5.33 | 7.08 | 8.01 |

As shown in Table 6, it was found: that the same tendency as Test Example 4 was obtained; that Formulation Example 19 comprising neither crospovidone nor carmellose sodium had the longest disintegration time, and then, the order of the disintegration time was Formulation Example 18 (6 parts by mass of carmellose sodium)>Formulation Example 16 (6 parts by mass of crospovidone)>Formulation Example 17 (20 parts by mass of crospovidone); and that the order of the compression pressure to obtain the tablets was Formulation Example 18>Formulation Example 19>Formulation Example 16>Formulation Example 17. According to the present studies, it was demonstrated that crospovidone is more useful for the improvement of disintegration and formability, in comparison to the case of adding the same amount of carmellose sodium.

[Test Example 6] Absorption Test

Film coated tablets of Formulation Example 20 (comprising 20 mg of Compound A) and Formulation Example 21 (comprising 4 mg of Compound A), in which both tablets comprised Compound A and sodium lauryl sulfate, and the content of Compound A was different from each other, were prepared, and were then subjected to the same absorption test as Test Example 2.

Formulation Example 20

A film coating solution consisting of 6.8 g of a coating agent and 81.2 g of purified water was sprayed onto 180 g of the tablets obtained in Formulation Example 19, using a coater (FREUND CORPORATION), so as to obtain the film coated tablet of Formulation Example 20. As a coating agent, a common coating agent consisting of hypromellose, polyethylene glycol, titanium oxide and a coloring agent was used.

Formulation Example 21

12 g of Compound A, 12 g of sodium lauryl sulfate (NIKKOL SLS, manufactured by Nikko Chemicals Co., Ltd.), 354 g of lactose, and 138 g of corn starch were mixed with one another in a polyethylene bag for 1 minute. The total amount of the obtained mixture was sieved through a sieve with an opening of 500 m, and the resultant was then blended again in a polyethylene bag for 1 minute. The obtained mixed powders were placed in a fluidized bed granulator (Powrex Corporation), and granulated while 239 g of 7.5% low viscosity hydroxypropyl cellulose was sprayed thereon, so as to obtain a granulated material. The total amount of the obtained granules was sieved through a sieve with an opening of 850 m.

Thereafter, 20 g of microcrystalline cellulose and 2 g of magnesium stearate were added to 178 g of the sieved granules, followed by blending in a polyethylene bag. The obtained mixture was tableted in a tableting machine (KIKUSUI SEISAKUSHO LTD.) to obtain tablets. A film coating solution consisting of 6.8 g of a coating agent and 81.2 g of purified water was sprayed onto 180 g of the obtained tablets, using a coater (FREUND CORPORATION), so as to obtain the film coated tablet of Formulation Example 21.

These formulation examples were subjected to an absorption test as follows.

<Absorption Experiment Conditions>
Animals: Beagle dogs (KITAYAMA LABES CO., LTD., 6 male dogs)
Meal conditions: Fasting for 20 hours from previous day
Dose: 20 mg/body
Administration sample: Formulation Examples 20 and 21
Administration method: Oral administration with 50 mL of water
Pre-treatment: Thirty minutes before administration of the administration sample, atropine sulfate solution for intravenous injection (10 μg/0.1 mL/kg) and pentagastrin solution for intramuscular injection (10 μg/0.1 mL/kg) were intravenously or intramuscularly administered to the dogs respectively, and thereafter, the pentagastrin solution for intramuscular injection (10 µg/0.1 mL/kg) was intramuscularly administered thereto, twice, with an interval of 45 minutes.

Thirty minutes, 1 hour, 1.5 hours, 2 hours, 4 hours, and 8 hours after the oral administration of Formulation Examples 20 and 21, blood samples were collected from each animal, and the blood concentration of Compound A were measured (according to liquid chromatography/mass spectrometry), and the AUC, Cmax and Tmax values were then calculated. The results are shown in Table 7.

TABLE 7

|  | Formulation Example | |
| --- | --- | --- |
| (Unit: part by mass) | 20 | 21 |
| Compound A | 1 | 1 |
| Sodium lauryl sulfate | 1 | 1 |
| Lactose hydrate | 4.3 | 29.5 |
| Corn starch | 2.3 | 11.5 |
| Low viscosity hydroxypropyl cellulose | 0.3 | 1.5 |
| Microcrystalline cellulose | 1 | 5 |
| Magnesium stearate | 0.1 | 0.5 |
| Hypromellose | 0.3 | 1.5 |
| Polyethylene glycol | | |
| Titanium oxide | | |
| Coloring agent | | |
| Total | 10.3 | 51.5 |
| AUC ng · hr/mL | 1174 ± 233 | 971 ± 250 |
| Cmax ng/mL | 343 ± 86 | 281 ± 102 |
| Tmax hr | 3.7 ± 0.8 | 2.3 ± 1.4 |

From the results of Table 7, it was found that both the 20 mg tablet (Formulation Example 20) and the 4 mg tablet (Formulation Example 21) exhibited absorption without problems in the dogs. When comparing the properties of the two types of tablets, it was indicated that the 20 mg tablet was a formulation with slow Tmax, whereas the 4 mg tablet was a formulation that was relatively immediately absorbed, although its Tmax values varied.

[Test Example 7] Disintegration Test

In order to find out a pharmaceutical formulation having a small variation in Tmax values and immediately absorption, the tablets of Formulation Examples 22 to 32, the compositions of which are shown in Table 8, were prepared as follows, and the types and the amounts of extra additives to be added into granulated products comprising Compound A and sodium lauryl sulfate were evaluated. The disintegration was evaluated according to a disintegration test using water as a test solution. The results are shown in Table 8.

Formulation Example 22

60 g of Compound A, 60 g of sodium lauryl sulfate (NIKKOL SLS, manufactured by Nikko Chemicals Co., Ltd.), 258 g of lactose, and 138 g of corn starch were mixed with one another in a polyethylene bag for 1 minute. The total amount of the obtained mixture was sieved through a sieve with an opening of 500 µm, and the resultant was blended again in a polyethylene bag for 1 minute. The obtained mixed powders were placed in a fluidized bed granulator (Powrex Corporation), and then granulated while 241 g of 7.5% low viscosity hydroxypropyl cellulose was sprayed thereon, so as to obtain granules. The total amount of the obtained granules was sieved through a sieve with an opening of 850 m.

Thereafter, lactose hydrate (Super Tab 11SD, DFE Pharma), microcrystalline cellulose (CEOLUS pH-102, Asahi Kasei Corporation), crospovidone (Kollidon CL, BASF Corporation), and magnesium stearate were added to the obtained granules, and the obtained mixture was blended in a glass bottle to obtain mixture for compression. Using a universal tensile/compression testing machine (Shimadzu Corporation), 500 g of tablets were produced.

Formulation Example 23

D-mannitol (Pearlitol 100SD, manufactured by Roquette), microcrystalline cellulose (CEOLUS pH-102), crospovidone (Kollidon CL), and magnesium stearate were added to the granules obtained in the same manner as Formulation Example 22, and the obtained mixture was then blended in a glass bottle to obtain mixture for compression. Using a universal tensile/compression testing machine (Shimadzu Corporation), 500 g of tablets were produced.

Formulation Example 24

Microcrystalline cellulose (CEOLUS pH-102), crospovidone (Kollidon CL), and magnesium stearate were added to the granules obtained in the same manner as Formulation Example 22, and the obtained mixture was then blended in a glass bottle to obtain mixture for compression. Using a universal tensile/compression testing machine (Shimadzu Corporation), 300 g of tablets were produced.

Formulation Example 25

D-mannitol (Pearlitol 100SD), microcrystalline cellulose (CEOLUS KG-802, manufactured by Asahi Kasei Corporation), crospovidone (Kollidon CL), and magnesium stearate were added to the granules obtained in the same manner as Formulation Example 22, and the obtained mixture was then blended in a glass bottle to obtain mixture for compression. Using a universal tensile/compression testing machine (Shimadzu Corporation), 500 g of tablets were produced.

Formulation Example 26

D-mannitol (Pearlitol 100SD), microcrystalline cellulose (CEOLUS KG-802), crospovidone (Kollidon CL-SF), and magnesium stearate were added to the granules obtained in the same manner as Formulation Example 22, and the obtained mixture was then blended in a glass bottle to obtain mixture for compression. Using a universal tensile/compression testing machine (Shimadzu Corporation), 300 g of tablets were produced.

Formulation Example 27

D-mannitol (Pearlitol 100SD), microcrystalline cellulose (CEOLUS KG-802), crospovidone (Kollidon CL-SF), and magnesium stearate were added to the granules obtained in the same manner as Formulation Example 22, and the obtained mixture was then blended in a glass bottle to obtain mixture for compression. Using a universal tensile/compression testing machine (Shimadzu Corporation), 300 g of tablets were produced.

Formulation Example 28

D-mannitol (Pearlitol 100SD), microcrystalline cellulose (CEOLUS KG-802), crospovidone (Kollidon CL-SF), and magnesium stearate were added to the granules obtained in the same manner as Formulation Example 22, and the obtained mixture was then blended in a glass bottle to obtain mixture for compression. Using a universal tensile/compression testing machine (Shimadzu Corporation), 400 g of tablets were produced.

Formulation Example 29

D-mannitol (Pearlitol 100SD), microcrystalline cellulose (CEOLUS KG-802), crospovidone (Kollidon CL-SF), and magnesium stearate were added to the granules obtained in the same manner as Formulation Example 22, and the obtained mixture was then blended in a glass bottle to obtain mixture for compression. Using a universal tensile/compression testing machine (Shimadzu Corporation), 400 g of tablets were produced.

Formulation Example 30

D-mannitol (Pearlitol 100SD), microcrystalline cellulose (CEOLUS KG-802), crospovidone (Kollidon CL-SF), and magnesium stearate were added to the granules obtained in the same manner as Formulation Example 22, and the obtained mixture was then blended in a glass bottle to obtain mixture for compression. Using a universal tensile/compression testing machine (Shimadzu Corporation), 500 g of tablets were produced.

Formulation Example 31

D-mannitol (Pearlitol 100SD), microcrystalline cellulose (CEOLUS KG-802), and magnesium stearate were added to the granules obtained in the same manner as Formulation Example 22, and the obtained mixture was then blended in a glass bottle to obtain mixture for compression. Using a universal tensile/compression testing machine (Shimadzu Corporation), 500 g of tablets were produced.

Formulation Example 32

Mannitol (Pearlitol 100SD), microcrystalline cellulose (CEOLUS pH-102), and magnesium stearate were added to the granules obtained in the same manner as Formulation Example 22, and the obtained mixture was then blended in a glass bottle to obtain mixture for compression. Using a universal tensile/compression testing machine (Shimadzu Corporation), 500 g of tablets were produced.

TABLE 8

| (Unit: part by mass) | Formulation Example | | | | | | | | | | |
|---|---|---|---|---|---|---|---|---|---|---|---|
| | 22 | 23 | 24 | 25 | 26 | 27 | 28 | 29 | 30 | 31 | 32 |
| Compound A | 20 | 20 | 20 | 20 | 20 | 20 | 20 | 20 | 20 | 20 | 20 |
| Sodium lauryl sulfate | 20 | 20 | 20 | 20 | 20 | 20 | 20 | 20 | 20 | 20 | 20 |
| Lactose monohydrate | 86 | 86 | 86 | 86 | 86 | 86 | 86 | 86 | 86 | 86 | 86 |
| Corn starch | 46 | 46 | 46 | 46 | 46 | 46 | 46 | 46 | 46 | 46 | 46 |
| Low viscosity hydroxypropyl cellulose | 6 | 6 | 6 | 6 | 6 | 6 | 6 | 6 | 6 | 6 | 6 |
| Lactose monohydrate | 217 | — | — | — | — | — | — | — | — | — | — |
| D-mannitol | — | 217 | — | 217 | 74 | 59 | 158 | 138 | 242 | 267 | 267 |
| Microcrystalline cellulose CEOLUS PH-102 | 50 | 50 | 89 | — | — | — | — | — | — | — | 50 |
| CEOLUS KG-802 | — | — | — | 50 | 30 | 30 | 40 | 40 | 50 | 50 | — |
| Crospovidone | 50 | 50 | 30 | 50 | 15 | 30 | 20 | 40 | 25 | — | — |
| Magnesium stearate | 5 | 5 | 3 | 5 | 3 | 3 | 4 | 4 | 5 | 5 | 5 |
| Total | 500 | 500 | 300 | 500 | 300 | 300 | 400 | 400 | 500 | 500 | 500 |
| Tablet diameter (mm) | 11 | 11 | 10 | 11 | 9 | 9 | 10 | 10 | 11 | 11 | 11 |
| Compression pressure (kN) | 24 | 12 | 8 | 14 | 7.5 | 7.5 | 9 | 9 | 11 | 10 | 10 |
| Hardness (N) | 80 | 96 | 71 | 105 | 89 | 90 | 107 | 105 | 120 | 98 | 97 |
| Disintegration time, water (min:sec) | 2:51 | 1:34 | 3:28 | 1:34 | 4:30 | 4:19 | 3:29 | 4:27 | 3:12 | 9:17 | 7:36 |

First, the influence of addition of lactose monohydrate and D-mannitol was evaluated. As a result, as shown in the results of Formulation Examples 22 and 23, etc., the disintegration of the tablets in water was significantly improved by addition of D-mannitol.

Subsequently, the grade of microcrystalline cellulose and the influence of addition of crospovidone were evaluated. As a result, as shown in the results of Formulation Examples 23 and 25 and Formulation Example 31 and 32, etc., the grade of microcrystalline cellulose hardly affected on the disintegration of the tablets. On the other hand, from the results of Formulation Examples 25, 30 and 31, etc., it was demonstrated that addition of crospovidone largely contributes to the improvement of disintegration property.

Finally, the influence of the additive amounts of D-mannitol, microcrystalline cellulose and crospovidone was comprehensively evaluated. As a result, the disintegration time of all of Formulation Examples 26 to 30 was longer than that of Formulation Example 25. The disintegration of Formulation Example 27 (extra addition amount: 122 mg, crospovidone: 10%), Formulation Example 29 (extra addition amount: 222 mg, crospovidone: 10%) and Formulation Example 30 (extra addition amount: 322 mg, crospovidone: 5%) was inferior to that of Formulation Example 25 (extra addition amount: 322 mg, crospovidone: 10%). Accordingly, it was suggested that the total amount of extra additives necessary for preparing a tablet having rapid disintegration is approximately 1.5 times the amount of a granulated product, and further that the disintegrant (crospovidone) needs to be added in an amount of approximately 10% based on the mass of the tablet.

Test Example 8

The tablets of Formulation Examples 33 and 34 each comprising 20 mg of Compound A, in which the amount of the extra additive was different from one another, and the tablet of Formulation Example 35 comprising 4 mg of Compound A, were prepared as follows, and in vivo absorption was evaluated similarly as Test Example 2. The results are shown in Table 9.

Formulation Example 33

80 g of Compound A, 80 g of sodium lauryl sulfate (NIKKOL SLS, manufactured by Nikko Chemicals Co., Ltd.), 108 g of lactose, and 120 g of corn starch were mixed with one another in a polyethylene bag for 1 minute. The total amount of the obtained mixture was sieved through a sieve with an opening of 500 μm, and the resultant was blended again in a polyethylene bag for 1 minute. The obtained mixture were placed in a fluidized bed granulator (Powrex Corporation), and then granulated while 241 g of 7.5% low viscosity hydroxypropyl cellulose was sprayed thereon, so as to obtain a granules. The total amount of the obtained granules was sieved through a sieve with an opening of 850 μm.

Thereafter, 137 g of D-mannitol (Pealitol 100SD), 30 g of microcrystalline cellulose (CEOLUS KG-802), 30 g of crospovidone (Kollidon CL), and 3 g of magnesium stearate were added to 100 g of the sieved granules, followed by blending in a polyethylene bag. The obtained mixture was tableted in a tableting machine (KIKUSUI SEISAKUSHO LTD.) to obtain tablets. A film coating solution consisting of 7.7 g of a coating agent and 92.3 g of purified water was sprayed onto 180 g of the obtained tablets, using a coater (FREUND CORPORATION), so as to obtain the film coated tablet of Formulation Example 33. As a coating agent, a common coating agent consisting of hypromellose, polyethylene glycol, titanium oxide and a coloring agent was used.

Formulation Example 34

To 125 g of the sieved product of the granules obtained in the same manner as Formulation Example 33, 72.5 g of D-mannitol (Pealitol 100SD), 25 g of microcrystalline cellulose (CEOLUS KG-802), 25 g of crospovidone(Kollidon CL), and 2.5 g of magnesium stearate were added, and mixed with one another in a polyethylene bag. Thereafter, the obtained mixture was tableted in a tableting machine (KIKUSUI SEISAKUSHO LTD.) to obtain tablets. A film coating solution consisting of 7.2 g of a coating agent and 86.4 g of purified water was sprayed onto 180 g of the obtained tablets, using a coater (FREUND CORPORATION), so as to obtain the film coated tablet of Formulation Example 34.

Formulation Example 35

To 60 g of the sieved product of the granules obtained in the same manner as Formulation Example 33, 129.6 g of D-mannitol (Pealitol 100SD), 24 g of microcrystalline cellulose (CEOLUS KG-802), 24 g of crospovidone (Kollidon CL), and 2.4 g of magnesium stearate were added, and mixed with one another in a polyethylene bag. Thereafter, the obtained mixture was tableted in a tableting machine (KIKUSUI SEISAKUSHO LTD.) to obtain tablets. A film coating solution consisting of 7.5 g of a coating agent and 90.4 g of purified water was sprayed onto 180 g of the obtained tablets, using a coater (FREUND CORPORATION), so as to obtain the film coated tablet of Formulation Example 35.

These formulation examples were subjected to an absorption test as follows.

<Absorption Experiment Conditions>
Animals: Beagle dogs (KITAYAMA LABES CO., LTD., 6 male dogs)
Meal conditions: Fasting for 20 hours from previous day
Dose: 20 mg/body
Administration sample: Formulation Examples 33, 34, and 35
Administration method: Oral administration with 50 mL of water
Pre-treatment: Thirty minutes before administration of samples, atropine sulfate solution for intravenous injection (10 μg/0.1 mL/kg) and pentagastrin solution for intramuscular injection (10 μg/0.1 mL/kg) were intravenously or intramuscularly administered to the dogs respectively, and thereafter, the pentagastrin solution for intramuscular injection (10 μg/0.1 mL/kg) was intramuscularly administered twice, with an interval of 45 minutes.

Thirty minutes, 1 hour, 2 hours, 3 hours, 4 hours, 6 hours, and 8 hours after the oral administration of Formulation Examples 33, 34, and 35, blood samples were collected from each animal, and the blood concentration of Compound A were measured (according to liquid chromatography/mass spectrometry), and the AUC, Cmax and Tmax values were calculated. The results are shown in Table 9.

TABLE 9

| (Unit: part by mass) | Formulation Example 33 | Formulation Example 34 | Formulation Example 35 |
|---|---|---|---|
| Compound A | 1 | 1 | 1 |
| Sodium lauryl sulfate | 1 | 1 | 1 |
| Lactose monohydrate | 1.4 | 1.4 | 1.4 |
| Corn starch | 1.5 | 1.5 | 1.5 |
| Low viscosity hydroxypropyl cellulose | 0.15 | 0.15 | 0.15 |
| D-mannitol | 6.9 | 2.9 | 10.8 |
| Microcrystalline cellulose | 1.5 | 1 | 2 |
| Crospovidone | 1.5 | 1 | 2 |
| Magnesium stearate | 0.15 | 0.1 | 0.2 |
| Hypromellose Polyethylene glycol Titanium oxide Coloring agent | 0.45 | 0.3 | 0.6 |
| Total | 15.5 | 10.3 | 20.6 |
| AUC ng · hr/mL | 887 ± 121 | 856 ± 241 | 767 ± 194 |
| Cmax ng/mL | 263 ± 34 | 266 ± 84 | 234 ± 54 |
| Tmax hr | 2.3 ± 1.9 | 2.0 ± 1.3 | 2.0 ± 1.1 |

As shown in Table 9, the Tmax value tended to shorten in all formulation examples, and any differences in the PK profiles were not found. Therefore, it was demonstrated that all formulation examples provided formulation compositions having a small variation in the Tmax values and immediate absorption.

Test Example 9

A granules not comprising sodium alkyl sulfate was prepared as follows, and the influence of sodium alkyl sulfate on the process of producing the granulated material was evaluated. The results are shown in Table 10.

Formulation Example 36

60 g of Compound A, 60 g of sodium lauryl sulfate, 81 g of lactose, and 90 g of corn starch were sieved through a screen with an opening of 1700 µm, and placed in a fluidized bed granulator (Freund Corporation). Thereafter, the mixture was granulated, while 180 g of 5% low viscosity hydroxypropyl cellulose was sprayed thereon, so as to obtain granules.

Comparative Example 18

60 g of Compound A, 141 g of lactose, and 90 g of corn starch were sieved through a screen with an opening of 1700 µm, and placed in a fluidized bed granulator (Freund Corporation). Thereafter, a granulation step while spraying 5% low viscosity hydroxypropyl cellulose was intended to be performed. However, powders did not flow in the container, and could not be granulated.

Comparative Example 19

30 g of Compound A, 70.5 g of lactose, and 45 g of corn starch were sieved through a screen with an opening of 1700 µm, and placed in a fluidized bed granulator (Freund Corporation). Before the spraying of a binding liquid, water was sprayed to fluidize the mixture. Thereafter, the mixture was granulated, while spraying 90 g of 5% low viscosity hydroxypropyl cellulose, so as to obtain a granulated material.

Evaluation of Physical Properties of Powders

The mixed powders before granulation of Formulation Example 36 and Comparative Example 19 were evaluated using Powder Tester (HOSOKAWA MICRON CORPORATION), for the physical properties of the powders (repose angle, collapse angle, bulk density, tapped density, and compressibility index). The results are shown in Table 10.

TABLE 10

| (Unit: part by mass) | Formulation Example 36 | Comparative Example 18 | Comparative Example 19 |
|---|---|---|---|
| Compound A | 1 | 1 | 1 |
| Sodium lauryl sulfate | 1 | 0 | 0 |
| Lactose monohydrate | 1.35 | 2.35 | 2.35 |
| Corn starch | 1.5 | 1.5 | 1.5 |
| low viscosity hydroxypropyl cellulose | 0.15 | 0.15 | 0.15 |
| Total | 5 | 5 | 5 |
| Water spray before spraying of binding liquid | No | No | Yes |

TABLE 10-continued

| (Unit: part by mass) | Formulation Example 36 | Comparative Example 18 | Comparative Example 19 |
|---|---|---|---|
| Granulation | Possible | Impossible | Possible |
| Repose angle (°) | 48.6 | 54.8 | |
| Collapse angle (°) | 46.8 | 53.8 | |
| Bulk density (g/mL) | 0.28 | 0.3 | |
| Tapped density (g/mL) | 0.56 | 0.68 | |
| Compressibility index (%) | 50 | 55.9 | |

Regarding the physical properties of the powders, the test performed in accordance with international harmonization is described in "26. Fluidity of Powders" of the Japanese Pharmacopoeia 17th Edition. In this publication, compression index, bulk density (p bulk), and tapped density (p tapped) are defined as follows.

Compressibility index=(ρtapped−ρbulk)/ρtapped×100

Moreover, in the Japanese Pharmacopoeia 17th Edition, if referring to "Table 1. Flow Properties and Corresponding Angles of Repose", it is described that "when the angle of repose exceeds 50°, the flow is rarely acceptable for manufacturing purposes". Based on this description, when Formulation Example 36 is compared with Comparative Example 19, the repose angle is lower than 50° and is improved because of the presence of sodium lauryl sulfate. Hence, it was found that, in the present invention, addition of sodium alkyl sulfate including sodium lauryl sulfate provides the effects of a glidant.

Test Example 10

A granulated material not comprising sodium alkyl sulfate was tableted to prepare tablets as follows, and the effect of sodium alkyl sulfate on the manufacturing process of the tablets was evaluated.

Formulation Example 37

The total amount of the granules obtained in Formulation Example 36 was sieved through a sieve with an opening of 600 µm. 261.61 g of D-mannitol (Pearlitol 100SD), 48 g of microcrystalline cellulose (CEOLUS KG-802), 48 g of crospovidone (Kollidon CL), and 2.4 g of magnesium stearate were added to 120 g of the sievedgranules, and the mixture was blended in a polyethylene bag. Thereafter, the obtained mixture was tableted in a tableting machine (KIKUSUI SEISAKUSHO LTD.) to obtain tablets.

Comparative Example 20

Using the granules obtained in Comparative Example 19, tablets were obtained in the same manner as Formulation Example 37.

Evaluation of Ejection Pressure after Tableting

The tablets of Formulation Example 37 and Comparative Example 20 were evaluated in terms of the force required for ejecting the tablets from the tableting machine. The results are shown in FIG. 1.

During tableting for 60 minutes, the ejection force for Formulation Example 37 was constant, but the ejection force for Comparative Example 20 increased 5 minutes after the initiation of tableting, further increased over time until 30 minutes after the initiation of tableting, and thereafter a high ejection force was still needed.

The tablets of Formulation Example 37 and Comparative Example 20 were also compared with each other, in terms of the conditions of a die and a punch, at 30 minutes after the initiation of tableting. In both tablets, powders did not adhere to the punch, and no sticking was confirmed. However, in Comparative Example 20, the adhesion of powders to the die was observed. As such, many vertical streaks were confirmed on the lateral surface of the obtained tablets, and die friction as one of tableting failures occurred in the tablets of Comparative Example 20, that did not comprise sodium lauryl sulfate. In contrast, such die friction was not observed in Formulation Example 37.

From these results, it was found that, in the present invention, the addition of sodium alkyl sulfate, including sodium lauryl sulfate, provides the effect of improving die friction as one of tableting failures.

All publications, patents and patent applications cited in the present description are incorporated herein by reference in their entirety.

The invention claimed is:

1. A pharmaceutical composition comprising (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one having the following structure, or a pharmaceutically acceptable salt thereof, and sodium lauryl sulfate:

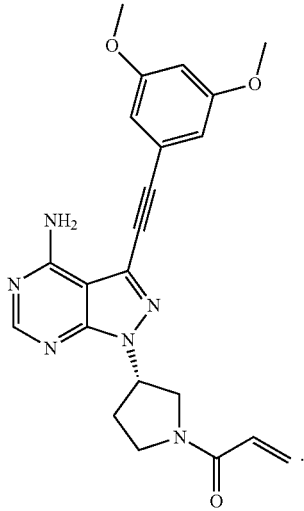

[Formula 1]

2. The composition according to claim 1, comprising sodium lauryl sulfate in a range of 0.05 to 15 parts by mass, relative to 1 part by mass of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one.

3. The composition according to claim 1, comprising sodium lauryl sulfate in a range of 0.2 to 5 parts by mass, relative to 1 part by mass of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one.

4. The composition according to claim 1, further comprising at least one compound selected from the group consisting of crospovidone, carmellose sodium, and carmellose calcium.

5. The composition according to claim 4, comprising crospovidone.

6. The composition according to claim 1, further comprising at least one compound selected from the group consisting of D-mannitol and lactose.

7. The composition according to claim 1, in the form of syrup, a powder, a granule, a tablet, or a capsule.

8. A method for producing a pharmaceutical composition comprising (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof, wherein the method comprises adding sodium lauryl sulfate to (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof.

9. The pharmaceutical composition according to claim 1, wherein said sodium lauryl sulfate is in an amount sufficient to increase the dissolution and/or absorption of said (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof.

10. The pharmaceutical composition according to claim 1, wherein said sodium lauryl sulfate is in an amount sufficient to increase the lubricative property and/or flowability of said (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one or a pharmaceutically acceptable salt thereof.

* * * * *